United States Patent
Swanson et al.

[11] Patent Number: 6,123,702
[45] Date of Patent: Sep. 26, 2000

[54] SYSTEMS AND METHODS FOR CONTROLLING POWER IN AN ELECTROSURGICAL PROBE

[75] Inventors: David K. Swanson; Robert Burnside, both of Mountain View; James G. Whayne, Saratoga; Dorin Panescu, Sunnyvale, all of Calif.

[73] Assignee: Scimed Life Systems, Inc., Maple Grove, Minn.

[21] Appl. No.: 09/150,830

[22] Filed: Sep. 10, 1998

[51] Int. Cl.$^7$ .................................................. A61B 18/04
[52] U.S. Cl. .................. 606/34; 606/42; 606/49
[58] Field of Search .......................... 606/34, 38, 41–42, 606/49, 50

[56] References Cited

U.S. PATENT DOCUMENTS

| | | |
|---|---|---|
| 4,181,131 | 1/1980 | Ogiu . |
| 4,493,320 | 1/1985 | Treat . |
| 4,532,924 | 8/1985 | Auth et al. . |
| 4,565,200 | 1/1986 | Cosman . |
| 4,567,890 | 2/1986 | Ohta et al. . |
| 4,681,122 | 7/1987 | Winters et al. . |
| 4,765,331 | 8/1988 | Petruzzi et al. . |
| 4,800,899 | 1/1989 | Elliott . |
| 4,860,744 | 8/1989 | Johnson et al. . |
| 4,907,589 | 3/1990 | Cosman . |
| 4,955,377 | 9/1990 | Lennox et al. . |
| 4,966,597 | 10/1990 | Cosman . |
| 4,998,933 | 3/1991 | Eggers et al. . |
| 5,013,312 | 5/1991 | Parins et al. . |
| 5,057,105 | 10/1991 | Malone et al. . |
| 5,069,223 | 12/1991 | McRae . |
| 5,078,716 | 1/1992 | Doll . |
| 5,108,391 | 4/1992 | Flachenecker et al. . |
| 5,122,137 | 6/1992 | Lennox . |
| 5,180,896 | 1/1993 | Gibby et al. . |
| 5,191,883 | 3/1993 | Lennox et al. . |
| 5,263,493 | 11/1993 | Avitall . |
| 5,277,201 | 1/1994 | Stern . |
| 5,282,840 | 2/1994 | Hudrlik .................................... 607/28 |
| 5,290,286 | 3/1994 | Parins . |
| 5,318,564 | 6/1994 | Eggers . |
| 5,341,807 | 8/1994 | Nardella . |
| 5,348,554 | 9/1994 | Imran et al. . |
| 5,370,650 | 12/1994 | Tovey et al. . |
| 5,383,876 | 1/1995 | Nardella . |
| 5,401,274 | 3/1995 | Kusunoki . |
| 5,403,342 | 4/1995 | Tovey et al. . |
| 5,423,810 | 6/1995 | Goble et al. . |
| 5,437,664 | 8/1995 | Cohen et al. . |
| 5,437,665 | 8/1995 | Munro . |
| 5,443,463 | 8/1995 | Stern et al. . |
| 5,451,224 | 9/1995 | Goble et al. . |
| 5,456,682 | 10/1995 | Edwards et al. .......................... 606/31 |
| 5,484,400 | 1/1996 | Edwards et al. . |
| 5,496,312 | 3/1996 | Klicek . |
| 5,505,730 | 4/1996 | Edwards . |
| 5,562,720 | 10/1996 | Stern et al. . |
| 5,562,721 | 10/1996 | Marchlinski et al. .................... 607/99 |
| 5,577,509 | 11/1996 | Panescu . |
| 5,630,426 | 5/1997 | Eggers et al. . |
| 5,681,282 | 10/1997 | Eggers et al. . |
| 5,683,366 | 11/1997 | Eggers et al. . |
| 5,697,536 | 12/1997 | Eggers et al. . |

(List continued on next page.)

FOREIGN PATENT DOCUMENTS

| | | |
|---|---|---|
| 0 484 671 A2 | 5/1992 | European Pat. Off. . |
| 0 584 787 A1 | 8/1992 | European Pat. Off. . |
| WO 93/06776 | 4/1993 | WIPO . |
| WO 94/10922 | 5/1994 | WIPO . |
| WO96/00036 | 1/1996 | WIPO . |
| WO 97/41793 | 11/1997 | WIPO . |

*Primary Examiner*—Linda C. M. Dvorak
*Assistant Examiner*—Roy Gibson
*Attorney, Agent, or Firm*—Henricks, Slavin & Holmes LLP

[57] ABSTRACT

Systems and methods for controlling the power supplied to an electrosurgical probe are disclosed. The systems and methods may be used to monitor electrode-tissue contact, adjust power in response to a loss of contact, and apply power in such a manner that charring, coagulum formation and tissue popping are less likely to occur.

33 Claims, 14 Drawing Sheets

U.S. PATENT DOCUMENTS

| | | |
|---|---|---|
| 5,697,882 | 12/1997 | Eggers et al. . |
| 5,697,909 | 12/1997 | Eggers et al. . |
| 5,702,386 | 12/1997 | Stern et al. . |
| 5,718,701 | 2/1998 | Shai et al. . |
| 5,733,280 | 3/1998 | Avitall . |
| 5,755,715 | 5/1998 | Stern et al. . |
| 5,836,943 | 11/1998 | Miller, III . |
| 5,906,314 | 5/1999 | Stern et al. .............................. 606/42 |
| 5,957,922 | 9/1999 | Imran ....................... 606/41 |

FIG. 12-A
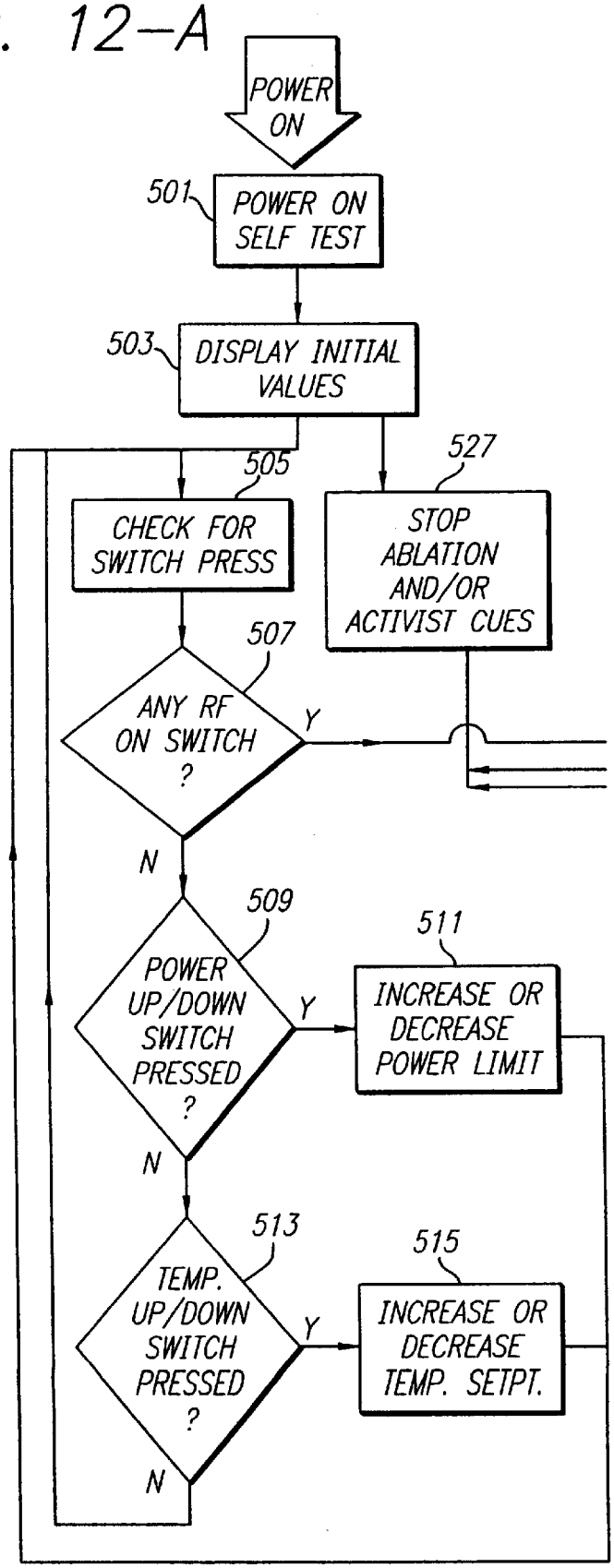

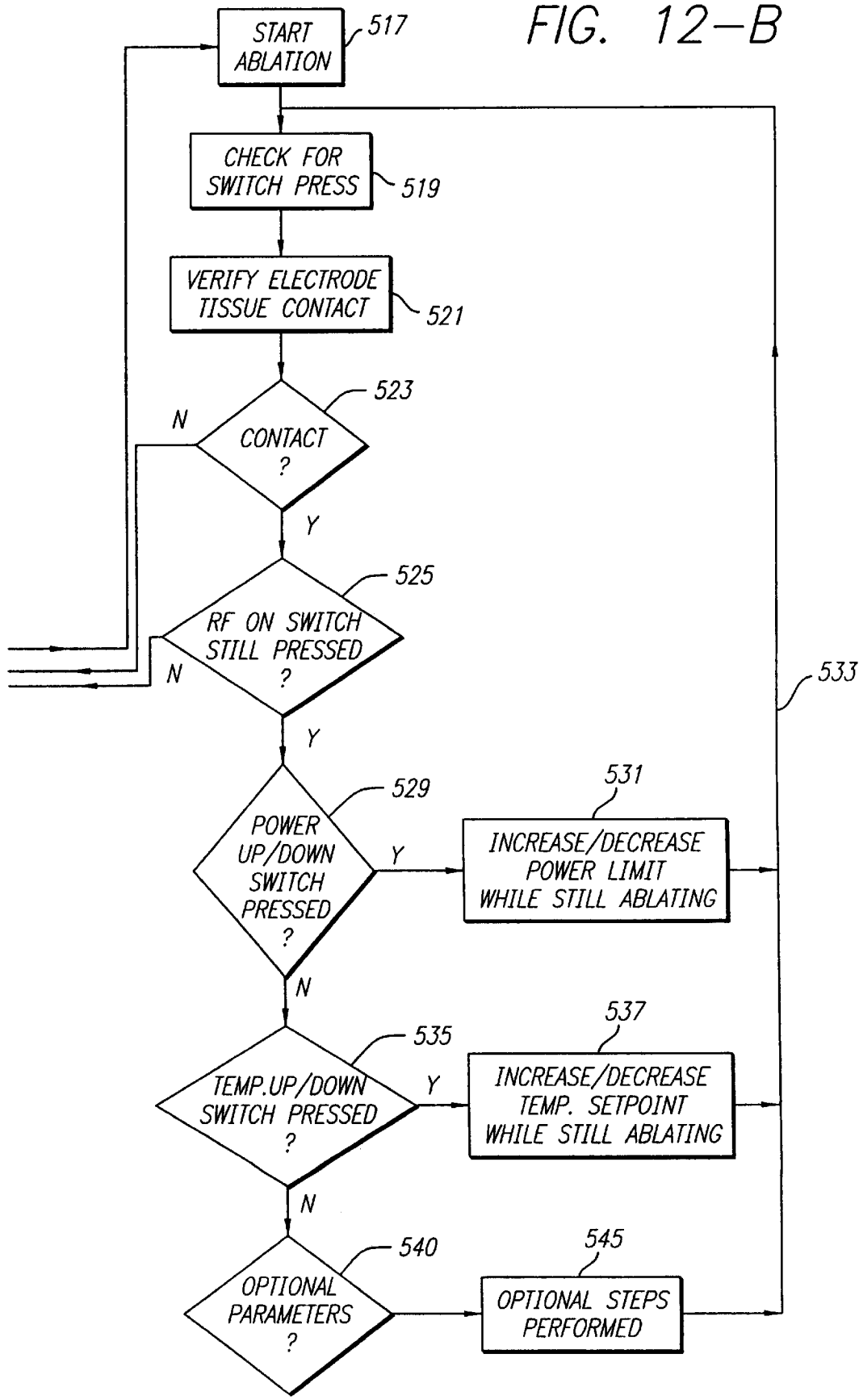
FIG. 12-B

SYSTEMS AND METHODS FOR CONTROLLING POWER IN AN ELECTROSURGICAL PROBE

BACKGROUND OF THE INVENTION

1. Field of Invention

The present invention relates generally to structures for positioning one or more diagnostic or therapeutic elements within the body and, more particularly, to power control systems for use with the same.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

Although pharmacological treatment is available for atrial fibrillation and flutter, the treatment is far from perfect. Many believe that the only way to treat the detrimental results of atrial fibrillation and flutter is to actively interrupt all of the potential pathways for atrial reentry circuits.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive. Thus, despite its considerable clinical success, only a few maze procedures are done each year.

More recently, maze-like procedures have been developed utilizing catheters and probes which can form lesions on the endocardium to effectively create a maze for electrical conduction in a predetermined path. Exemplary catheters are disclosed in commonly assigned U.S. Pat. No. 5,582,609. Exemplary surgical soft tissue coagulation probes employing a relatively shorter and stiffer shaft than a typical catheter are disclosed in commonly assigned U.S. patent application Ser. No. 08/949,117, filed Oct. 10, 1997, and U.S. patent application Ser. No. 09/072,835, filed May 5, 1998, both of which are incorporated by reference. Such probes may, for example, be used to treat atrial fibrillation in procedures wherein access to the heart is obtained by way of a thoracostomy, thoracotomy or median sternotomy.

Typically, the lesions are formed by ablating tissue with an electrode carried by the catheter or ablation probe. Electromagnetic radio frequency ("RF") energy applied by the electrode heats, and eventually kills (or "ablates") the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of denaturing proteins in tissue and heating the fluid within the tissue cell membranes which causes it to jell, thereby killing the tissue.

A primary goal of many soft tissue coagulation procedures is to create contiguous lesions (often long, curvilinear lesions) without over-heating tissue and causing coagulum and charring. Soft tissue coagulation occurs at 50° C., while over-heating occurs at 100° C. A problem in the related art is the issue of rapid turning on and off power when a coagulation electrode loses contact with tissue. Tissue in contact with a coagulation electrode acts as a load to the power circuit powering the electrode, usually an RF power circuit. When the coagulation electrode is pulled away from tissue or efficacious contact is lost, the load is removed, and the voltage output of the power circuit may change. Voltage may rise suddenly, which can cause problems when the electrode is reintroduced into contact with tissue, such as arcing or charring. As a safety consideration, the circuit in conventional systems is powered off for a predetermined period by turning off the power to the RF coagulation electrode when contact is lost.

However, the inventors herein have determined that powering a circuit completely off can result in a number of problems. For example, abrupt powering on of a coagulation electrode can char tissue if the voltage rise is too rapid. Additionally, powering a circuit completely off introduces the delay associated with powering the circuit back on into the procedure. Not only is this delay inconvenient, it can also be detrimental to the patient, especially since the loss of contact can happen many times during a procedure. For example, soft tissue coagulation probes can be used to perform a maze procedure during a mitral valve replacement, which requires cardiopulmonary bypass. The longer the patient is on bypass, the greater the likelihood of morbidity and mortality. Consequently, there is a need to quickly recover from a loss of electrode-tissue contact, without completely shutting off the power supply.

Another problem identified by the present inventors has been verifying that tissue is in contact with a coagulation electrode prior to or during a surgical or catheter-based procedure, which is generally termed electrode contact verification. This is a problem pervasive throughout all surgery being performed remotely, especially when direct visual line-of-sight is not present. The use of fluoroscopic techniques is somewhat inaccurate, and requires the use of human feedback. Accordingly, a need exists for an automated control system for electrode contact verification, and optionally with visual and/or audio feedback when there is loss of contact between the electrode and tissue.

Yet another problem identified by the present inventors is associated with tissue treatment efficacy when coagulating tissue. Specifically, because different tissues in the human body and between patients absorb energy at different rates, it is difficult to ascertain when proper tissue coagulation has been completed. Heretofore, ad hoc techniques have been used to determine when the soft tissue coagulation process has been completed. One technique is visual inspection. Another is applying coagulation energy for a predetermined period based on an estimate of the amount of time required to produce a therapeutic lesion. Such techniques are not always as reliable as desired. Thus, there is a need for accurately determining when tissue has been properly coagulated, so that coagulation may be automatically stopped.

SUMMARY OF THE INVENTION

Accordingly, the object of the present invention is to provide an apparatus for positioning an operative element (such as a coagulation electrode) within the body that avoids the aforementioned problems. Other operative elements include lumens for chemical or cryogenic coagulation, laser arrays, ultrasonic transducers, microwave electrodes, and D.C. hot wires.

In accordance with one advantageous aspect of a present invention, a power control system is provided which, in response to an indication that mechanical or efficacious contact between an electrode and tissue has been lost, will merely reduce the power to the electrode, rather than completely shut it off. In one embodiment, this is accomplished by ramping down the amplitude of a RF waveform supplied to the electrode to a lower level. Adjustment of the RF signal amplitude need not involve shutting off the RF power supply.

One exemplary method of determining when contact is lost involves the use of impedance measurements. Here, the impedance is measured and compared to an expected impedance. When the impedance is greater than the expected impedance, the RF source is driven to a relatively low voltage level, such as 5V, that allows safe continued operation and impedance measurement. When the measured impedance is less than the expected impedance, the RF source ramps up to the levels needed to reach the set temperature.

There are a number of advantages associated with such a system. For example, merely reducing voltage, as opposed to shutting it off completely, increases the speed at which probe-based maze procedures proceed by reducing the down time resulting from a loss of mechanical or efficacious electrode-tissue contact. In addition, when tissue contact resumes, voltage is ramped back up. As such, tissue damage due to an abrupt voltage rise is avoided.

In accordance with another present invention, a control system is provided which verifies electrode-tissue contact. Preferably, data are collected relating to variables that can be used by a processor for electrode contact verification. The data, which are sampled by the controller before and/or during the soft tissue coagulation process, may be temperature or tissue impedance data. For example, a rise in temperature over a predetermined period of time usually means that the electrode is in contact with tissue and is heating tissue rather than blood. Such a temperature rise may be measured prior to coagulation by applying a small amount of energy (less than that required for coagulation) to the tissue to verify contact. Conversely, a drop-off in temperature during coagulation may mean contact has been lost. In the case of impedance, a flat profile of impedance over frequency indicates that there is no tissue-electrode contact.

When it is determined from the data that efficacious electrode-tissue contact has been lost, the processor instructs the console to sound a visual or audio alarm. Voltage may also be ramped down as described above. In addition to the advantages related to power control and audio/visual feedback, this invention also reduces reliance on fluoroscopic techniques.

In accordance with another present invention, a control system is provided which determines when the soft tissue coagulation process is completed. In one embodiment, tissue impedance measurements are used to determine efficacious lesion formation. A change in the impedance versus frequency curve, from a sloping curve to a flat curve, indicates that tissue coagulation is completed. Temperature can also be used. Specifically, for a given coagulation energy level and time period, a predetermined temperature profile over time indicates that a lesion has been formed. As a result, coagulation procedures, especially those involving the formation of multiple therapeutic lesions, may be performed more efficiently.

In accordance with still another present invention, a control system is provided which brings the temperature at the electrode to a temperature that is less than the maximum set temperature, maintains that temperature at the electrode at this temperature for a predetermined period, and then increases the temperature at the electrode to the set temperature. In a preferred embodiment, the temperature at which tissue is maintained prior to ramping up may only be sufficient to create a transmural lesion in a relatively thin anatomical structure, while the set temperature is sufficient to create a transmural lesion in a relatively thick structure. Such a control system provides a number of important benefits. For example, in those instances where the tissue structure turns out to be relatively thin, a transmural lesion may be completed (and power delivery stopped) before the temperature reaches the set temperature because lower temperatures will be automatically used prior to reaching the set temperature. In other words, the system automatically attempts to form a lesion at a lower temperature before ramping up to the higher temperature. As many lesions will be formed at the lower temperature, coagulation procedures performed using the present control system are less likely to cause tissue charring and coagulum formation than procedures performed with conventional control systems.

The variable temperature set point system described in the preceding paragraph is also useful in epicardial applications where electrodes are placed on the epicardial surface of a heart chamber. Here, blood flow within the heart chamber produces a convective cooling effect on the heart surface and makes the creation of transmural lesions from the epicardial surface more difficult. As a result, higher temperatures (measured at the electrodes) or increased energy delivery duration is required to create a transmural lesion. Ramping the temperature to a temperature that is less than the maximum set temperature and maintaining that temperature for a predetermined period causes desiccation of the epicardial tissue and improves electrode/tissue contact. Then, when the temperature is increased to the maximum set temperature, tissue vaporization is less likely because the tissue is already desiccated. Conversely, when the temperature of tissue that has not been desiccated is suddenly increased from body temperature to the maximum set temperature required to make transmural lesions on the epicardial surface, vaporization commonly occurs. This can lead to perforation of the myocardium or the dislodgment of tissue.

Tissue coagulation depth can also be controlled by the varying the length of RF delivery. Longer RF applications usually produce deeper tissue coagulation.

In accordance with still another present invention, an interface is provided which audibly or visually indicates the status of the various aspects of the system such as, for example, ablation power, temperature, tissue/electrode contact, tissue impedance, time elapsed, type of electrode, and type of probe. In a preferred embodiment, the console may be driven by software that is modular and upgradeable to allow for new parameters to be displayed and monitored.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

FIG. 12 is a flowchart illustrating the steps for software operation of certain components in accordance with one embodiment of the present invention.

DETAILED DESCRIPTION OF THE PREFERRED EMBODIMENTS

The following is a detailed description of the best presently known mode of carrying out the invention. This description is not to be taken in a limiting sense, but is made merely for the purpose of illustrating the general principles of the invention.

The detailed description of the preferred embodiments is organized as follows:

I. Overview of the System

II. Electrosurgical Probe

III. Power Control

IV. Monitoring Tissue Contact, Coagulation Efficacy and Tissue Type

V. Variable Temperature Set Point

VI. User Interface System

The section titles and overall organization of the present detailed description are for the purpose of convenience only and are not intended to limit the present invention.

I. Overview of the System

Figure 1:
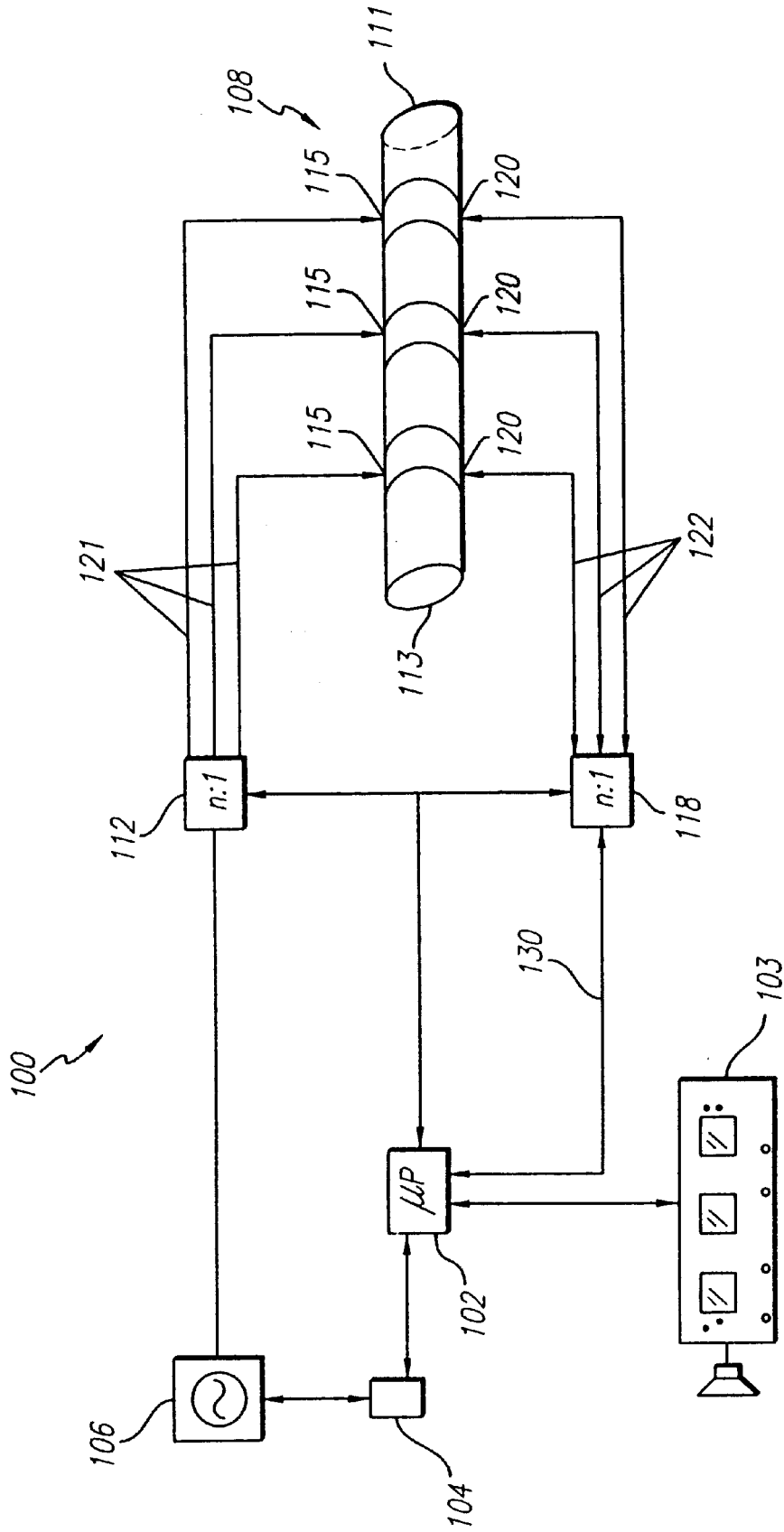
FIG. 1 is a schematic circuit block diagram of one embodiment of the present invention.

A schematic block circuit diagram of one preferred embodiment of the present invention is shown in FIG. 1. The exemplary system 100 employs a processor 102 to command the overall system. In the preferred embodiment, the processor is a microprocessor. However, any suitable controller, microcomputer, hardwired or preconfigured dedicated processor, or ASIC may be used for command and control. The processor 102 can have a separate and isolated power supply for safety purposes.

In the illustrated embodiment, the processor 102 is connected to an RF power supply controller 104, which regulates an AC power supply 106 that supplies RF power. RF power is preferably produced as a continuous sinusoidal waveform. However, other waveforms such as non-sinusoidal or pulsed can be used. RF power is received by a one-to-many power switching unit 112 for transmitting RF power to one or more electrode leads 121 that are attached to electrodes 115 on a probe 108. The selection of which electrodes 115 are supplied with RF energy by the power switching unit 112 is under the control of processor 102.

Figure 2:
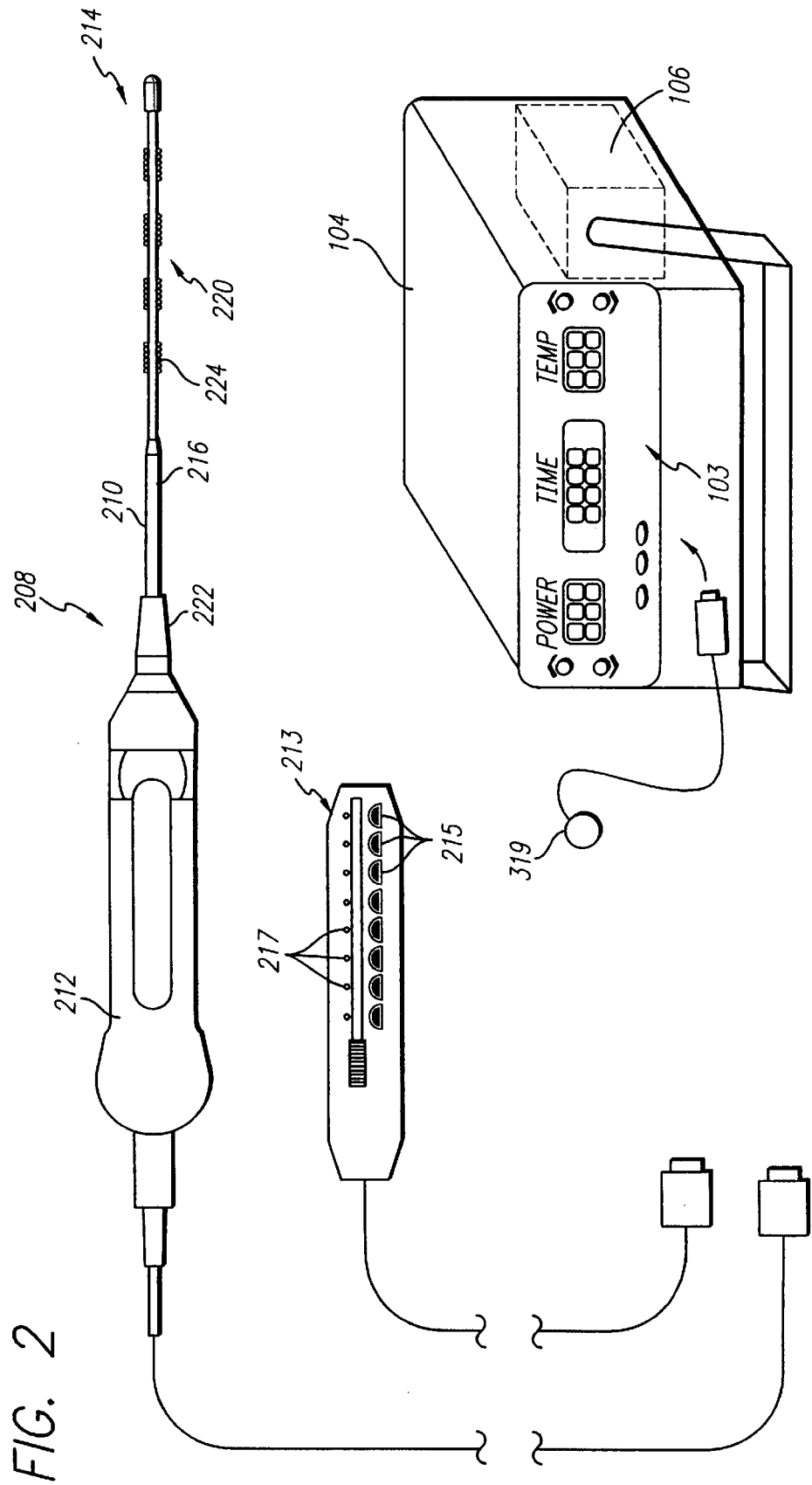
FIG. 2 is a perspective view of a tissue coagulation system in accordance with one embodiment of the present invention.

The processor 102 is also connected through suitable I/O lines to a console (or "user interface") 103, which may be part of a single unit that also includes the processor and power supply/control apparatus (see FIG. 2) or, alternatively, a separate device. The console 103 preferably includes keys, LED readouts, indicator lights, and audio and visual alarms. One example of a suitable user interface is illustrated in FIG. 2. A plurality of ports located on the console 103, and operably connected to the processor 102, may be used to connect the system 100 with other devices that may be used in a medical procedure.

The probe 108 may be any instrument capable of applying electro-magnetic energy, especially in the RF frequency range, including catheters, but preferably is a surgical probe such as those disclosed in U.S. patent applications Ser. No. 08/949,117, filed Oct. 10, 1997, and Ser. No. 09/072,835, filed May 5, 1998, both incorporated herein by reference. Ablation probe 108 has a distal end 111 and a proximal end 113 attached to a handle (shown in FIG. 2). Initiation of RF power to the electrodes on the probe can be accomplished through the use of a footswitch, a button on the probe handle, or a remote control device (as shown in FIG. 2 and discussed in Section II).

A number of sensor elements 120 reside on the probe 108 to measure data parameters relevant to the tissue being treated, such as tissue temperature. The sensors 120 are spaced apart from one another and are located on or near the electrodes 115. The sensors may be in the form of transducers, thermocouples, thermistors, or other collection electrodes. Sensors 120 receive data in analog form, which is converted to digital form. The data signals collected from sensors 120 are interfaced, signal conditioned, calibrated, range checked, converted from analog to digital and multiplexed at a signal conditioner, A/D converter and multiplex circuit unit 118, and received by processor 102 via I/O data signal line 130. The leads 121, 122 shown outside the probe 108 in FIG. 1 would in actual manufacture reside within the probe. For enhanced signal reconstruction, the processor 102 samples the sensors 120 to collect data at a frequency at least greater than the Nyquist sampling frequency.

With respect to the use of temperature sensors, details of a temperature controller and neural network for predicting temperature are described in Section III below. Once the coagulation procedure has started, the temperature sensors may be used to monitor the temperature setpoint, which is typically in a range from 50° to 100° C., and maintain the tissue temperature at the setpoint by increasing and decreasing power to the electrodes as needed. As described in detail below, data from the temperature sensors may also determine electrode-tissue contact and when a coagulation procedure is complete.

Turning to impedance, a flattening of the impedance versus frequency curve is either an indication of a lack of tissue contact, or an indication that the tissue is coagulated. Dedicated impedance electrodes may be provided on the probe. However, impedance is preferably monitored by simply measuring the voltage and current at different frequencies through the coagulating electrodes and dividing the measured voltage by the measured current. The level of current supplied to each electrode may also be used as a control parameter. These aspects of the exemplary embodiment are described in Sections IV and V below and in U.S. Pat. No. 5,577,509, which is incorporated herein by reference.

The RF source 106, processor 102, and sensors 120 form part of a negative feedback system for regulating RF power output to the electrodes. In the closed loop negative feedback system, the controller compares the sensor data (such as temperature, impedance or current data) with reference data stored in memory to generate an error signal. The processor interfaces with power supply controller 104 and RF source 106 (which may be combined into one circuit) to supply varying amounts of energy and power to the electrodes in order to decrease the error signal. Specifically, the RF source 106 is regulated to decrease the error signal.

Processes to determine whether the electrodes are in contact with tissue are preferably performed both before and during a coagulation procedure. These processes are discussed in Section IV below. Should the processor determine that there is a lack of sufficient contact, the level of power to the electrodes 115 will not be increased to the level required for ablation and, if desired, an audible and/or visual alarm will be activated by the processor 102 in order to inform the physician that the electrodes should be repositioned.

Upon detection of suitable contact between the electrodes 115 and tissue, the processor 102 instructs the RF power supply 106 and/or RF power supply controller 104 to supply power to the electrodes. In one embodiment the initial power setting for the apparatus is at 100 W power at about 500 kHz, with a maximum of about 150 W power.

When processor 102 senses that the electrodes 115 have lost contact with tissue or are no longer in close enough proximity for efficacious treatment, power to the electrodes is reduced (but not completely cut-off). Power may either be reduced to all of the electrodes, or only to those electrodes that have lost contact with tissue. The processor may use either temperature or impedance measurements to make this determination. Preferably, power is reduced by ramping down the amplitude of the RF energy source. Additionally, a visual or audible alarm may be provided to inform the physician that contact has been lost and power reduced. Once it is determined that contact or close proximity has been reestablished, the power level may be ramped back up.

II. Electrosurgical Probe

A preferred electrosurgical probe is shown by way of example in FIG. 2, and described in detail in the aforementioned U.S. patent application Ser. Nos. 08/949,117 and 09/072,835. The probe 208 includes a shaft 210 and a handle 212 towards the proximal section of the shaft. The shaft 210 consists of a hypo-tube, which is preferably either rigid or relatively stiff, and an outer polymer coating 216 over the hypo-tube. The handle 212 preferably consists of two molded handle halves and is also provided with strain relief element 222. An operative element 220 is provided on the distal section 214 of the shaft 210. In the illustrated embodiment, the operative element is in the form of a plurality of spaced electrodes 224, which are preferably either rigid ring-shaped electrodes or flexible helical electrodes.

The probe 208 may be used in a conventional electrosurgical system configuration, where power transmission from an RF generator (or other energy source) to the electrodes 224 is controlled by a footswitch. Nevertheless, and shown by way of example in FIG. 2, a manually operable remote control 213 having individual on-off switches 215 is preferably provided in conjunction with the probe 208. Similar switches may also be provided on the console 103. A global on-off switch (such as a footswitch, a switch on the handle 212, or a switch on the remote control 213) may also be provided to allow the physician using the apparatus to selectively enable and disable the supply of RF energy to electrodes 224. The individual on-off switches 215 allow the physician to selectively control the supply of power to individual electrodes. The exemplary remote control 213, which has seven individual on-off switches 215, is preferably used in conjunction with a probe having seven electrodes. If, for example, the physician intends to ablate tissue with only three of the electrodes, then the three chosen electrodes may be enabled by way of the corresponding switches 215 prior to placing the global on-off switch in the ON position.

A plurality of indicator elements 217 are also provided on the exemplary remote control 213, as shown in FIG. 2. Preferably, there is one indicator element for each of the on-off switches 215. The indicator elements may also be in the form of indicator lights. Sound-based indications of the on-off status of the switches 215 may also be used. For example, a speaker on the handle or the power control apparatus may be employed to periodically indicate which of the switches 215 are in the ON position.

A plurality of temperature sensors (not shown in FIG. 2) may be located on, under, abutting the edges of, or in between, the electrode elements in any of the exemplary devices disclosed herein. Additionally, a reference temperature sensing element may be provided on the handle 212, the shaft 210, or within the power supply and control apparatus.

III. Power Control

A. General

Figure 3:
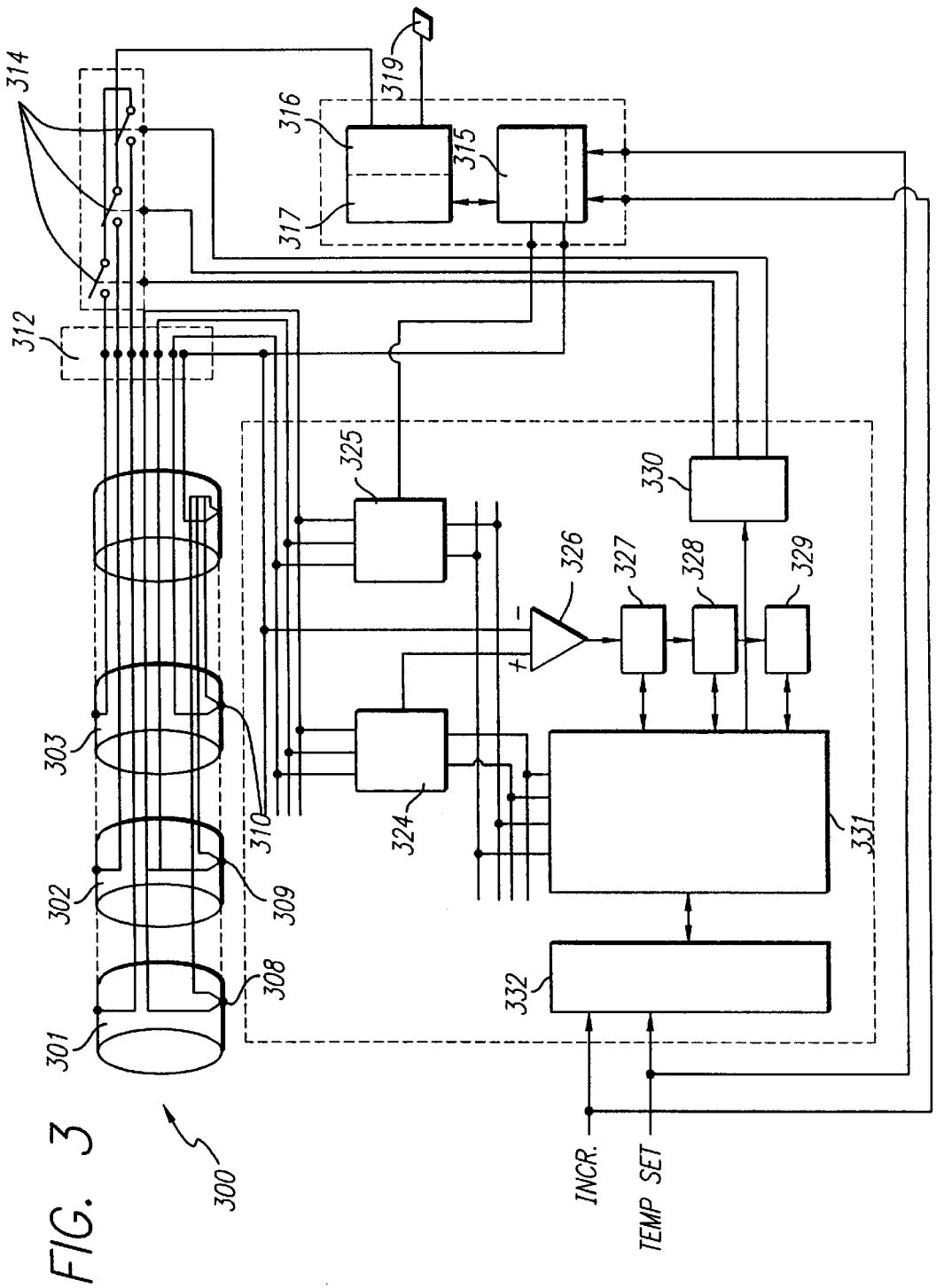
FIGS. 3 and 4 are schematic views of a system for controlling the application of ablating energy to multiple electrodes using multiple temperature sensors.

FIG. 3 shows, in schematic form, an exemplary system 300 for applying soft tissue coagulating (or "ablating") energy by multiple emitters based, at least in part, upon local temperature conditions sensed by multiple sensing elements.

In FIG. 3, the multiple sensing elements comprise thermocouples 308, 309, and 310 individually associated with the multiple emitters of energy, which comprise electrode regions 301, 302, and 303 (such as those located on the distal portion of the probe shown in FIG. 2). The system 300 also includes a common reference thermocouple 311 carried for exposure to the blood pool. The reference thermocouple can also be located on the probe handle or within the power control hardware. Alternatively, other kinds of temperature sensing elements can be used, like, for example, thermistors, fluoroptic sensors, and resistive temperature sensors, in which case the reference thermocouple 311 would typically not be required.

The system 300 further includes an indifferent electrode 319 for operation in uni-polar mode.

The electrode regions 301, 302, 303 can comprise the rigid electrode segments previously described. Alternatively, the electrode regions 301, 302, 303 can comprise a continuous or segmented flexible electrode of wrapped wire or ribbon. It should be appreciated that the system 300 can be used in association with any energy emitting element that employs multiple, independently actuated emitting elements.

The system 300 includes a source of energy 317, such as the RF energy sources described above with reference to FIGS. 1 and 2. The source 317 is connected (through a conventional isolated output stage 316) to an array of power switches 314, one for each electrode region 301, 302, and 303. A connector 312 (carried by the probe handle) electrically couples each electrode region 301, 303, 303 to its own power switch 314 and to other parts of the system 300.

The system 300 also includes a microcontroller 331 coupled via an interface 330 to each power switch 314. The microcontroller 331, which preferably corresponds to the processor 102 shown in FIG. 1, turns a given power switch 314 on or off to deliver RF power from the source 317 individually to the electrode regions 301, 302, and 303. The delivered RF energy flows from the respective electrode region 301, 302, and 303, through tissue, to the indifferent electrode 319, which is connected to the return path of the isolated output stage 316.

Figure 4:
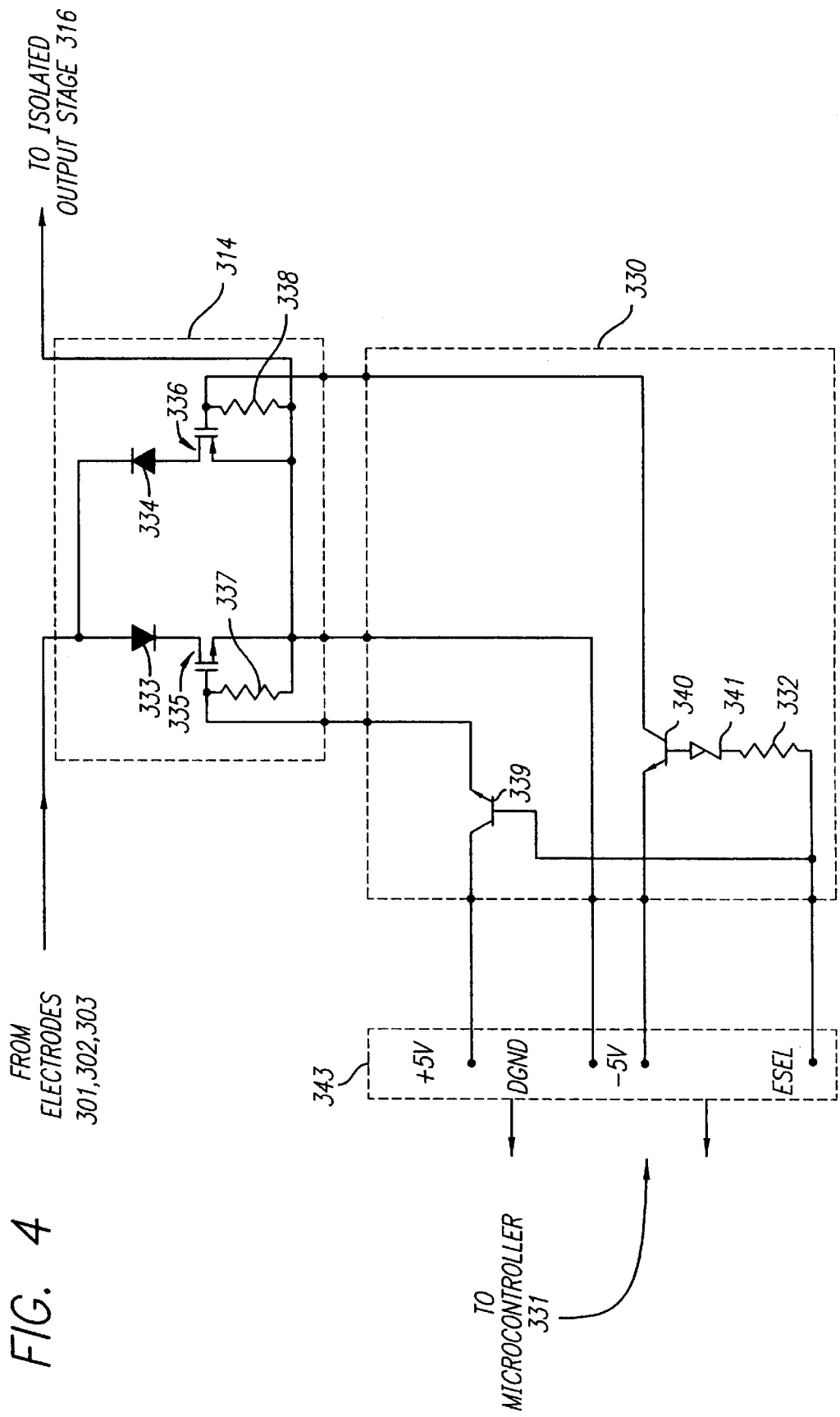

The power switch 314 and interface 330 configuration can vary according to the type of energy being applied. FIG. 4 shows a representative implementation for applying RF energy.

In this implementation, each power switch 314 includes an N-MOS power transistor 335 and a P-MOS power transistor 336 coupled in between the respective electrode region 301, 302, and 303 and the isolated output stage 316 of the power source 317.

A diode 333 conveys the positive phase of RF energy to the electrode region. A diode 334 conveys the negative phase of the RF energy to the electrode region. Resistors 337 and 338 bias the N-MOS and P-MOS power transistors 335 and 336 in conventional fashion.

The interface 330 for each power switch 314 includes two NPN transistors 339 and 340. The emitter of the NPN transistor 339 is coupled to the gate of the N-MOS power transistor 335. The collector of the NPN transistor 340 is coupled to the gate of the P-MOS power transistor 380.

The interface for each power switch 314 also includes a control bus 343 coupled to the microcontroller 331. The control bus 343 connects each power switch 314 to digital ground (DGND) of the microcontroller 331. The control bus 343 also includes a (+) power line (+5V) connected to the collector of the NPN transistor 339 and a (−) power line (−5V) connected to the emitter of the NPN interface transistor 340.

The control bus 343 for each power switch 314 further includes an $E_{SEL}$ line. The base of the NPN transistor 339 is coupled to the $E_{SEL}$ line of the control bus 343. The base of the NPN transistor 340 is also coupled the $E_{SEL}$ line of the control bus 343 via the Zener diode 341 and a resistor 332. $E_{SEL}$ line connects to the cathode of the Zener diode 341 through the resistor 332. The Zener diode 341 is selected so that the NPN transistor 340 turns on when $E_{SEL}$ exceeds about 3 volts (which, for the particular embodiment shown, is logic 1).

It should be appreciated that the interface 330 can be designed to handle other logic level standards. In the particular embodiment, it is designed to handle conventional TTL (transistor transfer logic) levels.

The microcontroller 331 sets $E_{SEL}$ of the control bus 343 either at logic 1 or at logic 0. At logic 1, the gate of the N-MOS transistor 335 is connected to (+) 5 volt line through the NPN transistors 339. Similarly, the gate of the P-MOS transistor 336 is connected to the (−) 5 volt line through the NPN transistor 340. This conditions the power transistors 335 and 336 to conduct RF voltage from the source 317 to the associated electrode region. The power switch 314 is "on."

When the microcontroller 331 sets $E_{SEL}$ at logic 0, no current flows through the NPN transistors 339 and 340. This conditions the power transistors 335 and 336 to block the conduction of RF voltage to the associated electrode region. The power switch 314 is "off."

The system 300 (see FIG. 3) further includes two analog multiplexers (MUX) 324 and 325. The multiplexers 324 and 325 receive voltage input from each thermocouple 308, 309, 310, and 311. The microcontroller 331 controls both multiplexers 324 and 325 to select voltage inputs from the multiple temperature sensing thermocouples 308, 309, 310, and 311.

The voltage inputs from the thermocouples 308, 309, 310, and 311 are sent to front end signal conditioning electronics. The inputs are amplified by differential amplifier 326, which reads the voltage differences between the copper wires of the thermocouples 308/309/310 and the reference thermocouple 311. The voltage differences are conditioned by element 327 and converted to digital codes by the analog-to-digital converter 328. The look-up table 329 converts the digital codes to temperature codes. The temperature codes are read by the microcontroller 331.

The microcontroller 331 compares the temperature codes for each thermocouple 308, 309, and 310 to preselected criteria to generate feedback signals. The preselected criteria are inputted through a user interface 332. In addition to temperature, and as discussed below, criteria such as power, impedance and current may also be used to generate feedback signals. These feedback signals control the interface power switches 314 via the interface 330, turning the electrodes 301, 302, and 303 off and on.

The other multiplexer 325 connects the thermocouples 308, 309, 310, and 311 selected by the microcontroller 331 to a temperature controller 315. The temperature controller 315 also includes front end signal conditioning electronics, as already described with reference to elements 326, 327, 328, and 329. These electronics convert the voltage differences between the copper wires of the thermocouples 308/309/310 and the reference thermocouple 311 to temperature codes. The temperature codes are read by the controller and compared to preselected criteria to generate feedback signals. These feedback signals control the amplitude of the voltage (or current) generated by the source 317 for delivery to the electrodes 301, 302, and 303.

Based upon the feedback signals of the microcontroller 331 and the temperature controller 315, the system 300 distributes power to the multiple electrode regions 301, 302, and 303 to establish and maintain a uniform distribution of temperatures along a lesion-forming element, such as the distal portion of the exemplary probe illustrated in FIG. 2. In this way, the system 300 obtains safe and efficacious lesion formation using multiple emitters of energy.

The system 300 can control the delivery of ablating energy in different ways. Representative modes will now be described.

B. Individual Amplitudes/Collective Duty Cycle

The electrode regions 301, 302, and 303 will be symbolically designated E(J), where J represents a given electrode region (J=1 to N).

As before described, each electrode region E(J) has at least one temperature sensing element 308, 309, and 310, which will be designated S(J,K), where J represents the electrode region and K represents the number of temperature sensing elements on each electrode region (K=1 to M).

Figure 5:
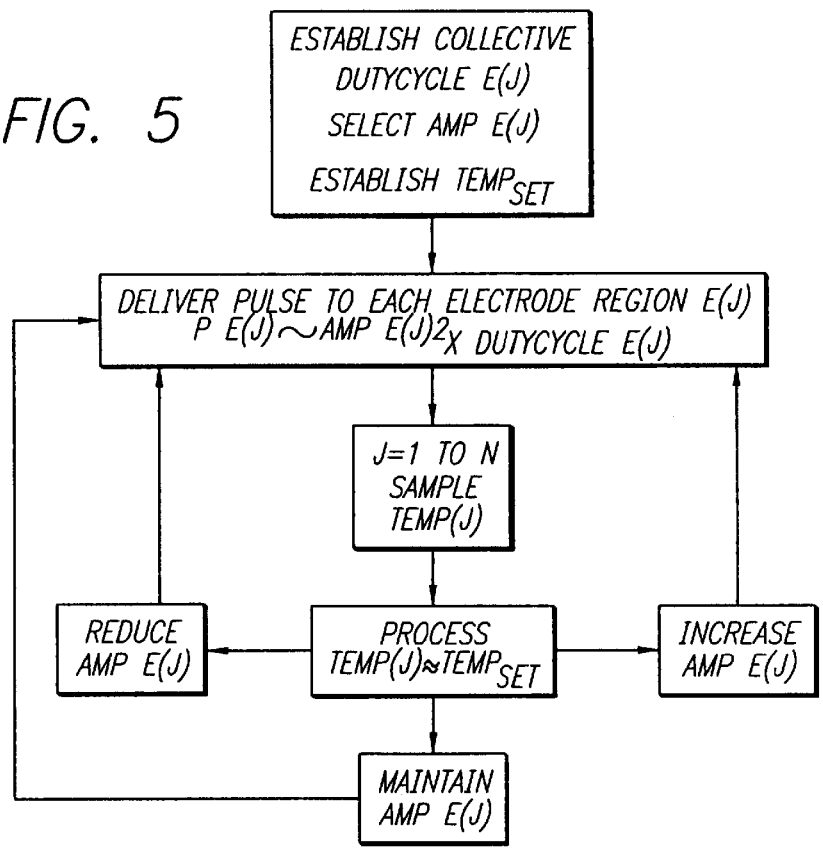
FIG. 5 is a schematic flow chart showing an implementation of the temperature feedback controller shown in FIGS. 3 and 4, using individual amplitude control with collective duty cycle control.

In this mode (see FIG. 5), the microcontroller 331 operates the power switch interface 330 to deliver RF power from the source 317 in multiple pulses of duty cycle 1/N.

With pulsed power delivery, the amount of power ($P_{E(J)}$) conveyed to each individual electrode is as follows:

$$P_{E(J)} \sim AMP_{E(J)}^2 \times DUTYCYCLE_{E(J)}$$

where:

$AMP_{E(J)}$ is the amplitude of the RF voltage conveyed to the electrode region E(J), and $DUTYCYCLE_{E(J)}$ is the duty cycle of the pulse, expressed as follows:

$$DUTYCYCLE_{E(J)} = TON_{E(J)}/[TON_{E(J)} + TOFF_{E(J)}]$$

where:

$TON_{E(J)}$ is the time that the electrode region E(J) emits energy during each pulse period, $TOFF_{E(J)}$ is the time that the electrode region E(J) does not emit energy during each pulse period.

The expression $TON_{E(J)} + TOFF_{E(J)}$ represents the period of the pulse for each electrode region E(J).

In this mode, the microcontroller 331 collectively establishes duty cycle ($DUTYCYCLE_{E(J)}$) of 1/N for each electrode region (N being equal to the number of electrode regions).

The microcontroller 331 may sequence successive power pulses to adjacent electrode regions so that the end of the duty cycle for the preceding pulse overlaps slightly with the beginning of the duty cycle for the next pulse. This overlap in pulse duty cycles assures that the source 317 applies power continuously, with no periods of interruption caused by open circuits during pulse switching between successive electrode regions.

In this mode, the temperature controller 315 makes individual adjustments to the amplitude of the RF voltage for each electrode region ($AMP_{E(J)}$), thereby individually changing the power $P_{E(J)}$ of energy conveyed during the duty cycle to each electrode region, as controlled by the microcontroller 331.

In this mode, the microcontroller 331 cycles in successive data acquisition sample periods. During each sample period, the microcontroller 331 selects individual sensors S(J,K), and voltage differences are read by the controller 315 (through MUX 325) and converted to temperature codes TEMP(J).

When there is more than one sensing element associated with a given electrode region, the controller 315 registers all sensed temperatures for the given electrode region and selects among these the highest sensed temperature, which constitutes TEMP(J).

In this mode, the controller 315 compares the temperature TEMP(J) locally sensed at each electrode E(J) during each data acquisition period to a set point temperature $TEMP_{SET}$ established by the physician. Based upon this comparison, the controller 315 varies the amplitude $AMP_{E(J)}$ of the RF voltage delivered to the electrode region E(J), while the microcontroller 331 maintains the $DUTYCYCLE_{E(J)}$ for that electrode region and all other electrode regions, to establish and maintain TEMP(J) at the set point temperature $TEMP_{SET}$.

The set point temperature $TEMP_{SET}$ can vary according to the judgment of the physician and empirical data. A representative set point temperature for cardiac ablation is believed to lie in the range of 40° C. to 95° C., with 70° C. being a representative preferred value.

The manner in which the controller 315 governs $AMP_{E(J)}$ can incorporate proportional control methods, proportional integral derivative (PID) control methods, or fuzzy logic control methods.

For example, using proportional control methods, if the temperature sensed by the first sensing element TEMP(1) >$TEMP_{SET}$, the control signal generated by the controller 315 individually reduces the amplitude $AMP_{E(1)}$ of the RF voltage applied to the first electrode region E(1), while the microcontroller 331 keeps the collective duty cycle $DUTYCYCLE_{E(1)}$ for the first electrode region E(1) the same. If the temperature sensed by the second sensing element TEMP(2)<$TEMP_{SET}$, the control signal of the controller 315 increases the amplitude $AMP_{E(2)}$ of the pulse applied to the second electrode region E(2), while the microcontroller 331 keeps the collective duty cycle $DUTYCYCLE_{E(2)}$ for the second electrode region E(2) the same as $DUTYCYCLE_{E(1)}$, and so on. If the temperature sensed by a given sensing element is at the set point temperature $TEMP_{SET}$, no change in RF voltage amplitude is made for the associated electrode region.

The controller 315 continuously processes voltage difference inputs during successive data acquisition periods to individually adjust $AMP_{E(J)}$ at each electrode region E(J), while the microcontroller 331 keeps the collective duty cycle the same for all electrode regions E(J). In this way, the mode maintains a desired uniformity of temperature along the length of the distal portion of the exemplary probe shown in FIG. 2 or other lesion-forming element.

Using a proportional integral differential (PID) control technique, the controller 315 takes into account not only instantaneous changes that occur in a given sample period, but also changes that have occurred in previous sample periods and the rate at which these changes are varying over time. Thus, using a PID control technique, the controller 315 will respond differently to a given proportionally large instantaneous difference between TEMP (J) and $TEMP_{SET}$, depending upon whether the difference is getting larger or smaller, compared to previous instantaneous differences, and whether the rate at which the difference is changing since previous sample periods is increasing or decreasing.

C. Collective Amplitude/individual Duty Cycles

Figure 6:
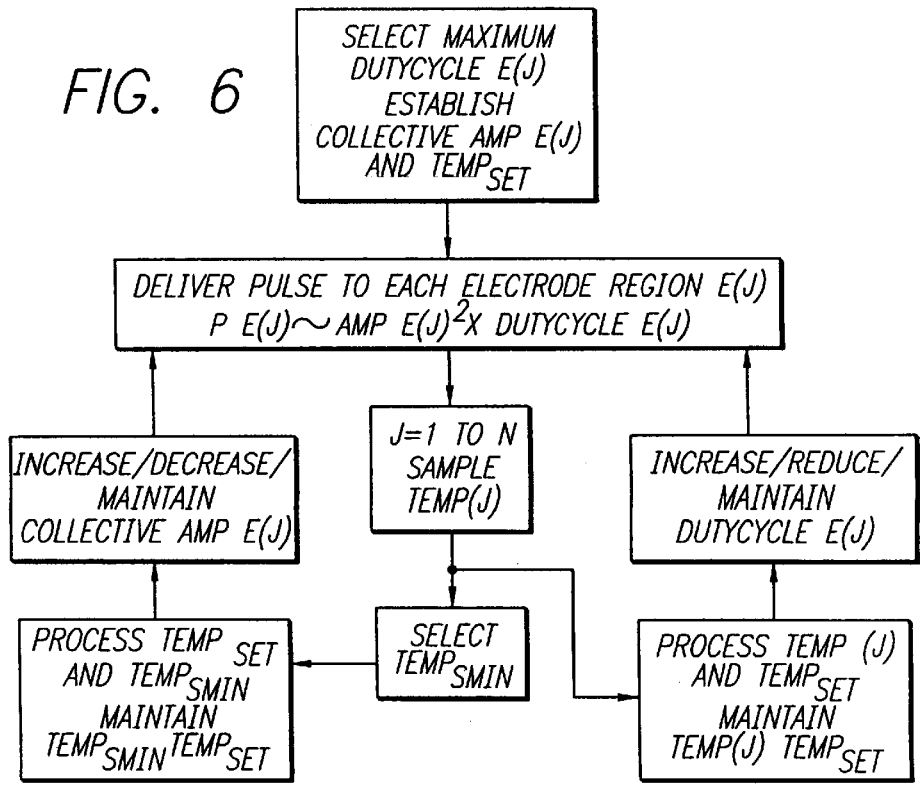
FIG. 6 is a schematic flow chart showing an implementation of the temperature feedback controller shown in FIGS. 3 and 4, using individual duty cycle control with collective amplitude control.

In this feedback mode (see FIG. 6), the controller 315 governs the source 317 to collectively control the RF voltage amplitude $AMP_{E(J)}$ for all electrode regions based upon the lowest local temperature sensed $TEMP_{SMIN}$. At the same time, in this feedback mode, the microcontroller 331 individually alters the power conveyed to the electrode regions where temperatures greater than $TEMP_{SMIN}$ are sensed, by adjusting the duty cycle $DUTYCYCLE_{E(J)}$ of these electrode regions.

In this mode, as in the previous mode, the microcontroller 331 separates the power into multiple pulses. Initially, each pulse has the same duty cycle ($DUTYCYCLE_{E(J)}$ of 1/N. As in the previous mode, the application of successive RF pulses to adjacent electrode regions may be timed to overlap so that the source 317 applies power continuously to the electrode regions E(J).

The controller 315 cycles in successive data acquisition periods to sequentially read the temperature sensed by each sensing element TEMP(J). When there are multiple sensing elements associated with each electrode region, the controller 315 registers all sensed temperatures for the particular electrode and selects among these the highest sensed temperature, which is TEMP(J).

In this mode, the controller 315 compares, during each data acquisition period, the individual temperatures sensed TEMP(J) to the set point temperature $TEMP_{SET}$. The controller 315 also selects the lowest sensed temperature $TEMP_{SMIN}$. The controller 315 adjusts $AMP_{E(J)}$ to maintain $TEMP_{SMIN}>>TEMP_{SET}$, using proportional, PID, or fuzzy logic control techniques. At the same time, the microcontroller 331 adjusts $DUTYCYCLE_{E(J)}$ of the electrode regions where TEMP(J)>$TEMP_{SMIN}$ to maintain TEMP(J) >> $TEMP_{SET}$.

For example, using only proportional control techniques, if $TEMP_{SMIN}<TEMP_{SET}$, the controller 315 collectively increases the amplitude of the RF voltage of all electrode regions, based upon the difference between $TEMP_{SMIN}$ and $TEMP_{SET}$ ($\Delta TEMP_{SMIN/SET}$), until $TEMP_{SMIN}>TEMP_{SET}$.

During this time (when $TEMP_{SMIN}$ remains below $TEMP_{SET}$), the microcontroller 331 also controls the application of power to the other electrode regions E(J) where the local sensed temperature TEMP(J) is above $TEMP_{SMIN}$, as follows:

(i) if TEMP(J)<$TEMP_{SET}$, the microcontroller 331 increases the duty cycle of the power applied to the electrode region E(J) at the RF voltage amplitude established by $\Delta TEMP_{SMIN/SET}$.

(ii) if TEMP(J)>$TEMP_{SET}$, the microcontroller 331 decreases the duty cycle of the power applied to the electrode region E(J) at the RF voltage amplitude established by $\Delta TEMP_{SMIN/SET}$.

(iii) if $TEMP(J)_{S(N)}=TEMP_{SET}$, the microcontroller 331 maintains the duty cycle for the given electrode region E(N) at the RF voltage amplitude established by $\Delta TEMP_{SMIN/SET}$.

When $TEMP_{SMIN}=TEMP_{SET}$, the controller 315 collectively reduces the RF voltage amplitude delivered to all electrode regions. When $TEMP_{SMIN}=TEMP_{SET}$, the controller 315 collectively maintains the then-established RF voltage amplitude delivered to all electrode regions.

D. Temperature Control with Hysteresis

Figure 7:
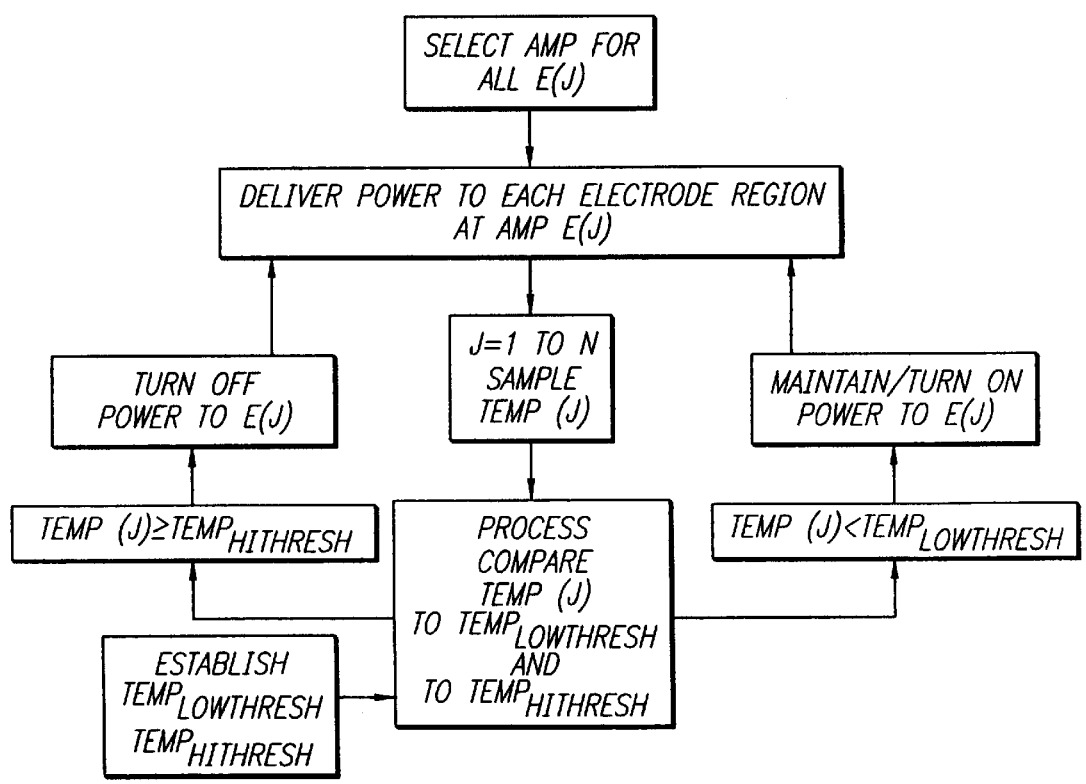
FIG. 7 is a schematic flow chart showing an implementation of the temperature feedback controller shown in FIGS. 3 and 4, using temperature control with hysteresis.

In this mode (see FIG. 7), as in the previous modes, the system 300 cycles in successive data acquisition periods to sequentially register the temperature sensed by the sensing elements TEMP(J) for the electrode regions E(J). As before, when there are multiple sensing elements associated with each electrode region, the system 300 registers all sensed temperatures for the particular electrode region and selects among these the highest sensed temperature, which becomes TEMP(J).

In this mode, the microcontroller 331 compares the temperature sensed locally at each electrode region TEMP(J) during each data acquisition period to high and low threshold temperatures $TEMP_{HITHRESH}$ and $TEMP_{LOWTHRESH}$, where $$TEMP_{HITHRESH}=TEMP_{SET}+INCR$$

$$TEMP_{LOWTHRESH}=TEMP_{SET}-INCR$$

where $TEMP_{SET}$ is the set point temperature, and

INCR is a preselected increment.

When operated in this mode, the microcontroller 331 operates the power switch interface 330 to turn a given electrode region E(J) off when the local temperature sensed at that electrode region TEMP(J)>$TEMP_{HITHRESH}$. The microcontroller 331 keeps the electrode region turned off until the locally sensed temperature TEMP(J) drops below $TEMP_{LOWTHRESH}$. The microcontroller 331 turns a given electrode region E(J) on and supplies power at a selected voltage amplitude when the local temperature sensed at that electrode region TEMP(J)<$TEMP_{LOWTHRESH}$.

The values for $TEMP_{SET}$ and INCR can vary according to the judgment of the physician and empirical data. As before stated, a representative value for $TEMP_{SET}$ is believed to lie in the range of 40° C. and 95° C., with a preferred value of 70° C. A representative value of INCR is believed to lie in the range of 2° C. to 8° C., with a preferred representative value of around 5° C.

In this implementation, the controller 315 establishes a constant RF voltage amplitude sufficiently high to maintain the desired temperature conditions during hysteresis. Alternatively, the controller 315 can have the capability to adjust voltage should the coolest sensed temperature $TEMP_{SMIN}$ decrease below a selected lower limit below $TEMP_{LOWTHRESH}$, or should the longest duty cycle exceed a predetermined value. It should be appreciated that there are other ways of adjusting and maintaining the amplitude while the hysteresis control method is carried out.

E. Differential Temperature Disabling

Figure 8:
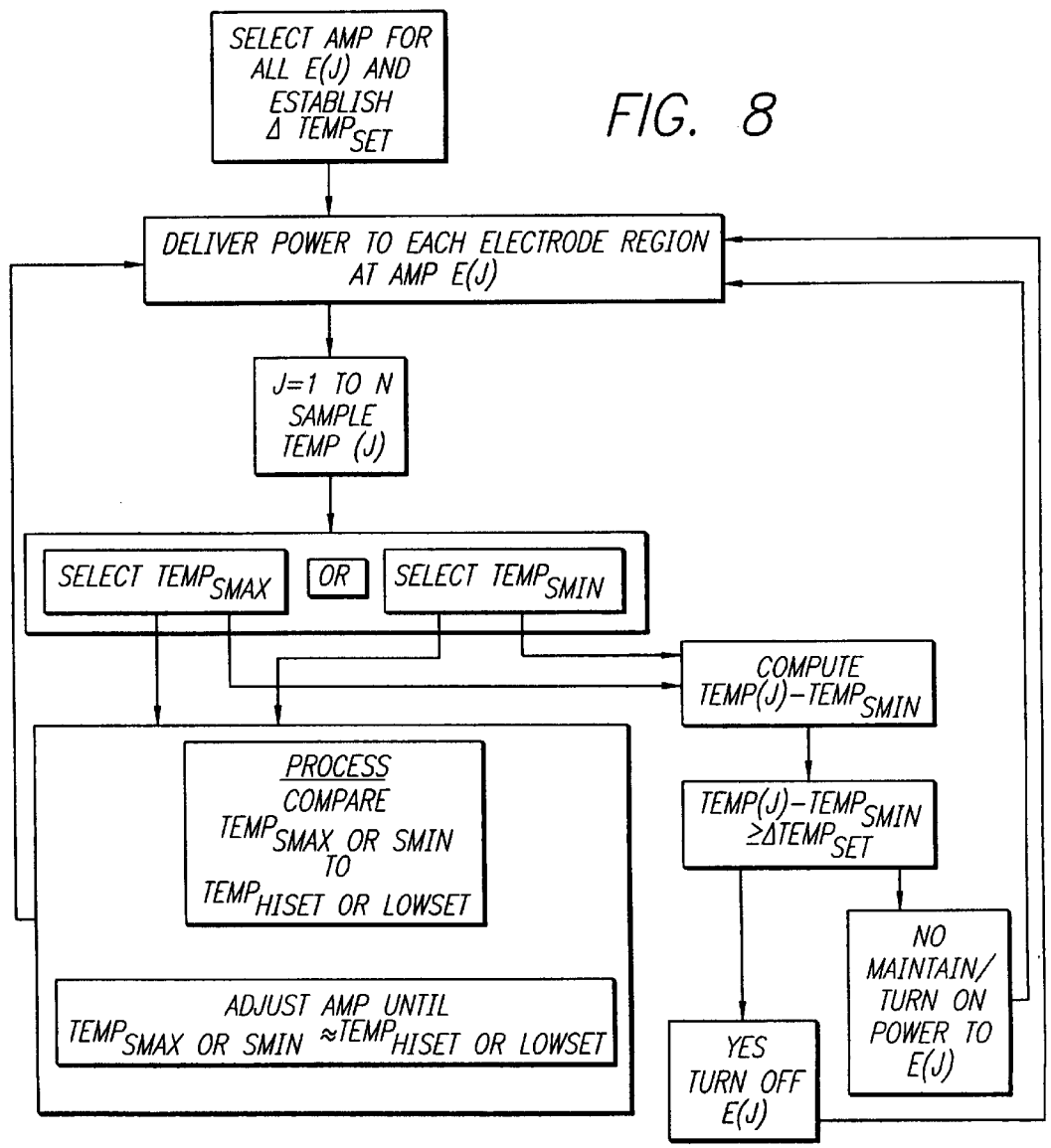
FIG. 8 is a schematic flow chart showing an implementation of the temperature feedback controller shown in FIGS. 3 and 4, using variable amplitude and differential temperature disabling.

In this mode (see FIG. 8), the temperature controller 315 selects at the end of each data acquisition phase the sensed temperature that is the greatest for that phase ($TEMP_{SMAX}$). The temperature controller 315 also selects for that phase the sensed temperature that is the lowest ($TEMP_{SMIN}$).

The controller 315 compares the selected hottest sensed temperature $TEMP_{SMAX}$ to a selected high set point temperature $TEMP_{HISET}$. The comparison generates a control signal that collectively adjusts the amplitude of the RF voltage for all electrodes using proportional, PID, or fuzzy logic control techniques.

In a proportion control implementation scheme:

(i) If $TEMP_{SMAX}>TEMP_{HISET}$, the control signal collectively decreases the amplitude of the RF voltage delivered to all electrode regions;

(ii) If $TEMP_{SMAX}<TEMP_{HISET}$, the control signal collectively increases the amplitude of the RF voltage delivered to all electrode regions;

(iii) If $TEMP_{SMAX}=TEMP_{HISET}$, no change in the amplitude of the RF voltage delivered to all electrode regions is made.

It should be appreciated that the temperature controller 315 can select for amplitude control purposes any one of the sensed temperatures $TEMP_{SMAX}$, $TEMP_{SMIN}$, or temperatures in between, and compare this temperature condition to a preselected temperature condition.

Working in tandem with the amplitude control function of the temperature controller 315, the microcontroller 331 governs the delivery of power to the electrode regions based upon difference between a given local temperature TEMP(J) and $TEMP_{SMIN}$. This implementation computes the difference between local sensed temperature TEMP(J) and $TEMP_{SMIN}$ and compares this difference to a selected set point temperature difference $D\ TEMP_{SET}$. The comparison generates a control signal that governs the delivery of power to the electrode regions.

If the local sensed temperature TEMP(J) for a given electrode region E(J) exceeds the lowest sensed temperature $TEMP_{SMIN}$ by as much as or more than $\Delta\ TEMP_{SET}$ (that is, if TEMP(J)–$TEMP_{SMIN}$>$\Delta TEMP_{SET}$), the microcontroller 331 turns the given electrode region E(J) off. The microcontroller 331 turns the given electrode E(J) back on when TEMP(J)–$TEMP_{SMIN}$<$\Delta TEMP_{SET}$.

Figure 9:
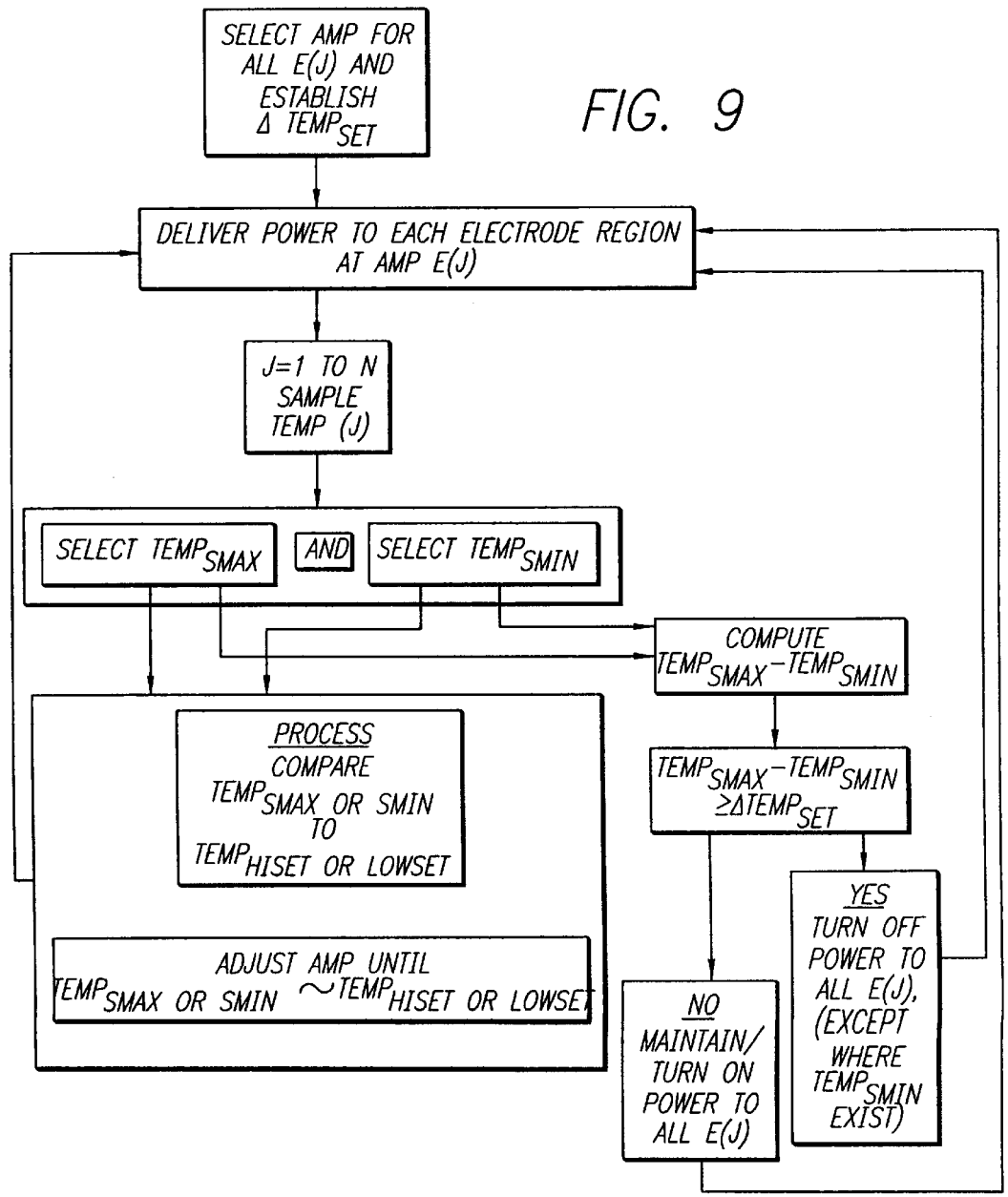
FIG. 9 is a schematic flow chart showing an implementation of the temperature feedback controller shown in FIGS. 3 and 4, using differential temperature disabling.

Alternatively (see FIG. 9), instead of comparing TEMP(J) and $TEMP_{SMIN}$, the microcontroller 331 can compare $TEMP_{SMAX}$ and $TEMP_{SMIN}$. When the difference between $TEMP_{SMAX}$ and $TEMP_{SMIN}$ equals or exceeds a predetermined amount $\Delta TEMP_{SET}$, the controller 331 turns all electrode regions off, except the electrode region where $TEMP_{SMIN}$ exists. The controller 331 turns these electrode regions back on when the temperature difference between $TEMP_{SMAX}$ and $TEMP_{SMIN}$ is less than $\Delta TEMP_{SET}$.

Some of the above-described temperature-based control schemes alter power by adjusting the amplitude of the RF voltage. It should be appreciated that, alternatively, power can be altered by the adjusting the amplitude of RF current. Therefore, the quantity $AMP_{E(J)}$ used in this Specification can mean either RF voltage amplitude or RF current amplitude.

F. Deriving Predicted Hottest Temperature

As previously described, a given electrode region can have more than one temperature sensing element associated with it. In the previously described control modes, the controller 315 registers all sensed temperatures for the given electrode region and selects among these the highest sensed temperature, which constitutes TEMP(J). There are alternative ways of making this selection. One way is to derive the predicted hottest temperature.

Because of the heat exchange between the tissue and the electrode region, the temperature sensing elements may not measure exactly the maximum temperature at the region. This is because the region of hottest temperature occurs beneath the surface of the tissue at a depth of about 0.5 to 2.0 mm from where the energy emitting electrode region (and the associated sensing element) contacts the tissue. If the power is applied to heat the tissue too quickly, the actual maximum tissue temperature in this subsurface region may exceed 100° C. and lead to tissue desiccation and/or microexplosion.

Figure 10:
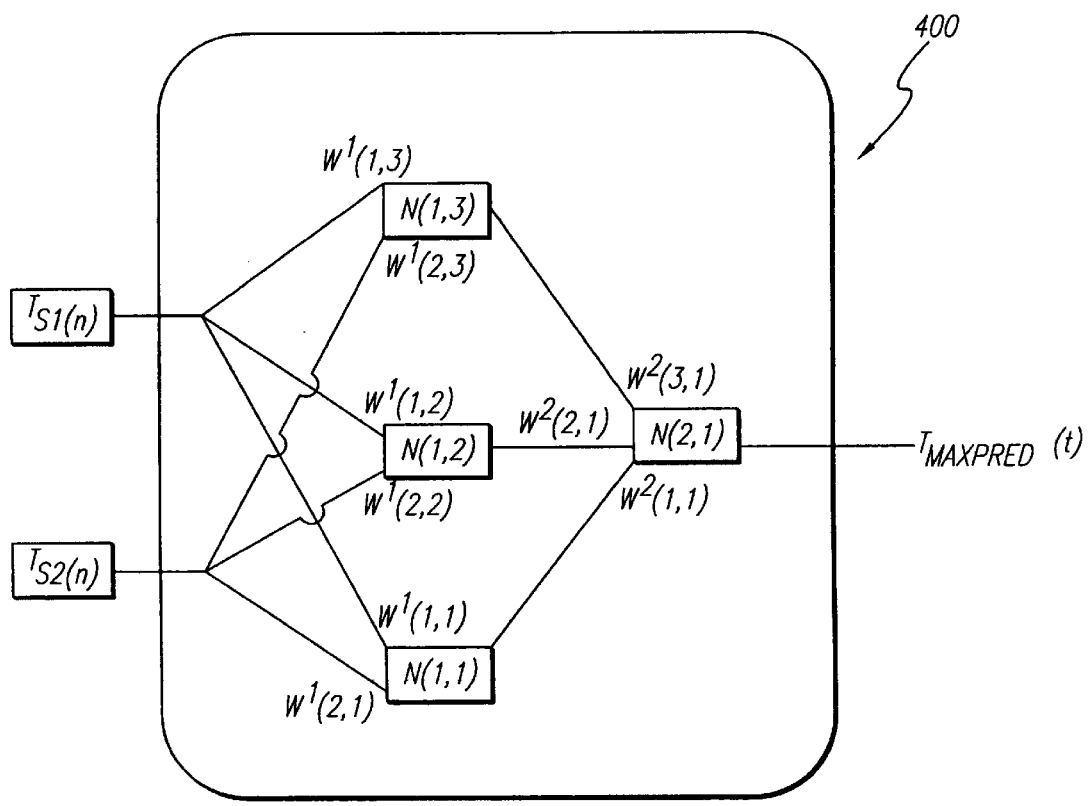
FIG. 10 is a schematic view of a neural network predictor, which receives as input the temperatures sensed by multiple sensing elements at a given electrode region and outputs a predicted temperature of the hottest tissue region.

FIG. 10 shows an implementation of a neural network predictor 400, which receives as input the temperatures sensed by multiple sensing elements S(J,K) at each electrode region, where J represents a given electrode region (J=1 to N) and K represents the number of temperature sensing elements on each electrode region (K=1 to M). The predictor 400 outputs a predicted temperature of the hottest tissue region $T_{MAXPRED}(t)$. The controller 315 and microcontroller 331 derive the amplitude and duty cycle control signals based upon $T_{MAXPRED}(t)$, in the same manners already described using TEMP(J).

The predictor 400 uses a two-layer neural network, although more hidden layers could be used. As shown in FIG. 10, the predictor 400 includes a first and second hidden layers and four neurons, designated $N_{(L,X)}$, where L identifies the layer 1 or 2 and X identifies a neuron on that layer. The first layer (L=1) has three neurons (X=1 to 3), as follows $N_{(1,1)}$; $N_{(1,2)}$; and $N_{(1,3)}$. The second layer (L=2) comprising one output neuron (X=1), designated $N_{(2,1)}$.

Temperature readings from the multiple sensing elements, only two of which—TS1(n) and TS2(n)—are shown for purposes of illustration, are weighed and inputted to each neuron $N_{(1,1)}$; $N_{(1,2)}$; and $N_{(1,3)}$ of the first layer. FIG. 10 represents the weights as $W^L_{(k,N)}$, where L=1; k is the input sensor order; and N is the input neuron number 1, 2, or 3 of the first layer.

The output neuron $N_{(2,1)}$ of the second layer receives as inputs the weighted outputs of the neurons $N_{(1,1)}$; $N_{(1,2)}$; and $N_{(1,3)}$. FIG. 10 represents the output weights as $W^L_{(O,X)}$, where L=2; O is the output neuron 1, 2, or 3 of the first layer; and X is the input neuron number of the second layer. Based upon these weighted inputs, the output neuron $N_{(2,1)}$ predicts $T_{MAXPRED}(t)$. Alternatively, a sequence of past reading samples from each sensor could be used as input. By doing this, a history term would contribute to the prediction of the hottest tissue temperature.

The predictor 400 must be trained on a known set of data containing the temperature of the sensing elements TS1 and TS2 and the temperature of the hottest region, which have been previously acquired experimentally. For example, using a back-propagation model, the predictor 400 can be trained to predict the known hottest temperature of the data set with the least mean square error. Once the training phase is completed the predictor 400 can be used to predict $T_{MAXPRED}(t)$.

The predicted tissue temperature can also be used to adjust the temperature set curve. For example, if the predictor 400 predicts a relatively high tissue temperature, then the temperature set curve can be adjusted downwardly and vice versa. The duration of an ablation procedure can also be adjusted based on predicted tissue temperature.

Other types of data processing techniques can be used to derive $T_{MAXPRED}(t)$. See, e.g., co-pending patent application Ser. No. 08/801,484, filed Feb. 18, 1997, and entitled "Tissue Heating and Ablation Systems and Methods Using Predicted Temperature for Monitoring and Control."

In addition to being used in the previously described temperature control systems, the predicted temperature of the hottest tissue region $T_{MAXPRED}(t)$ can be used in other power control systems or to adjust other power control parameters.

For example, $T_{MAXPRED}(t)$ may be used to adjust a temperature set point curve upwardly or downwardly. Either the entire curve, or just a portion thereof, may be adjusted. One example of such a temperature set point curve is the variable temperature set point curve discussed in Section V below. Another example is disclosed in U.S. Pat. No. 5,755,715, entitled "Tissue Heating and Ablation Systems and Methods Using Time-Variable Set Point Curves for Monitoring and Control." Adjusting a temperature set point curve upwardly will occur when $T_{MAXPRED}(t)$ is lower than the assumed maximum temperature that formed the basis for the set point curve. Such an adjustment will decrease the duration of the coagulation procedure, as compared to duration without the adjustment. The increase in speed is especially useful when the patient is on cardiopulmonary bypass.

Conversely, when $T_{MAXPRED}(t)$ is higher than the assumed maximum temperature, the temperature set point curve will be adjusted downwardly, thereby reducing the likelihood of undesired damage to ancillary tissue as well as charring or popping of the targeted tissue.

$T_{MAXPRED}(t)$ may also be used to increase or decrease the duration of a coagulation procedure. Adjusting a duration upwardly will occur when $T_{MAXPRED}(t)$ is lower than the assumed maximum temperature that formed the basis for the original duration estimation. This will insure that a therapeutic lesion will be formed. The duration of a coagulation procedure will be reduced when $T_{MAXPRED}(t)$ is higher than the assumed maximum temperature, thereby reducing the length of time that a patient is on bypass as well as the likelihood of undesired tissue damage.

IV. Monitoring Tissue Contact, Coagulation Efficacy and Tissue Type

In addition to maintaining a set temperature, electrode-tissue contact may also be monitored using the same process of sensing a variable (such as temperature, impedance or current), comparing it with a reference signal, and generating an error signal that may be used to control power output and audio/visual indicators on the console. The sensed data may also be used to make other determinations, such as tissue viability and tissue type. Preferably, all three of the determinations (i.e. contact, viability and type) will be made at at least one point during the coagulation procedure.

Figure 11A:
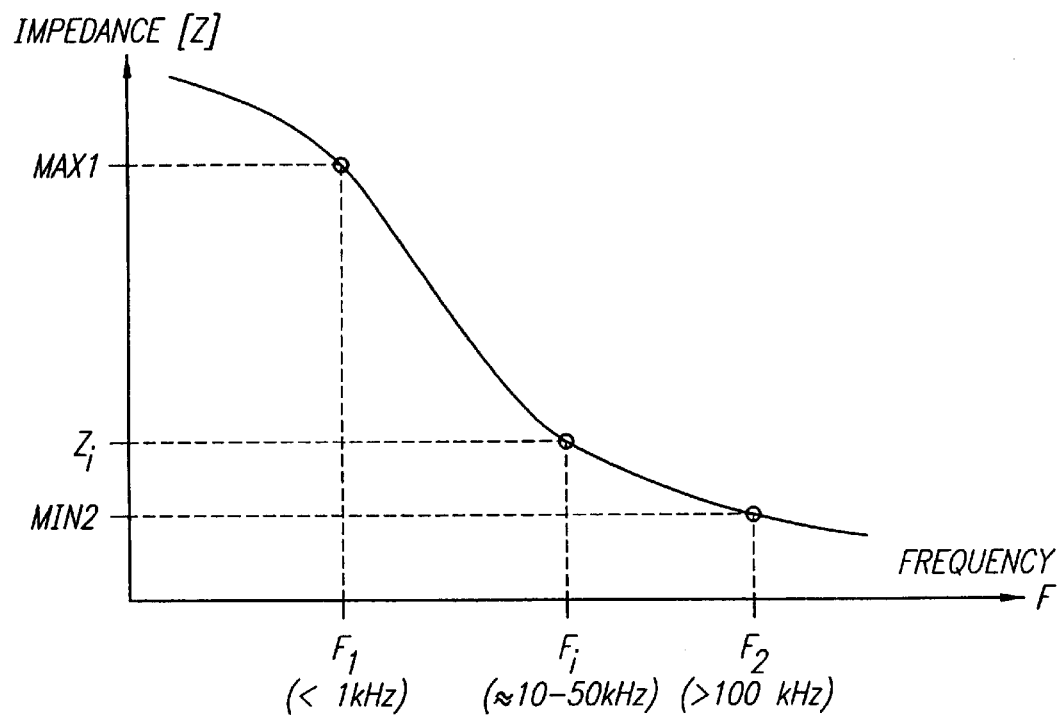
FIGS. 11(a), 11(b) and 11(c) are graphs illustrating impedance versus frequency.
Figure 11B:
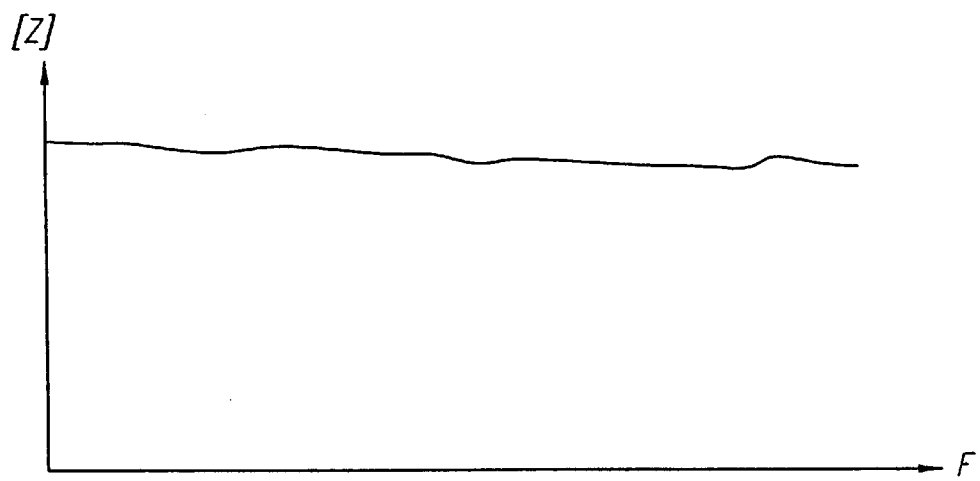
Figure 11C:
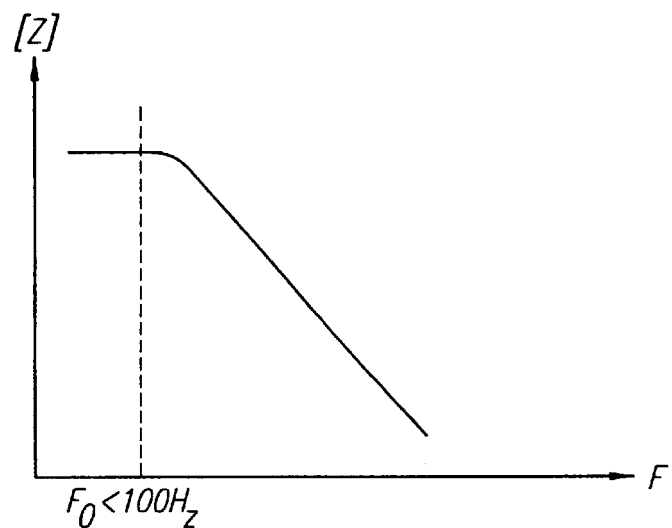

Turning first to impedance, the graph illustrated in FIG. 11(a) is representative of the impedance magnitude versus frequency curve for viable tissue, while the graph illustrated in FIG. 11(b) is representative of the curve for coagulated tissue or an instance where there is insufficient contact between the electrodes and tissue and the electrode is in blood, and the graph illustrated in FIG. 11(c) is representative of the curve when the electrodes are in air.

For viable tissue, there is a generally downward sloping curve as frequency increases, having a relative maximum point MAX1 at frequency f1 (about 1 kHz) and a relative minimum point MIN2 at frequency f2 (about 100 kHz). Under normal circumstances, the curve flattens out, as shown in FIG. 11(b), when the tissue is coagulated. However, the relatively flat curve is also indicative of a situation where the electrode tissue contact has been lost and the sensing electrodes are surrounded by blood. The processor could be used to take derivatives of the impedance curve to ascertain whether a change in the curve has occurred. Alternatively, the processor may be used to compare the difference between the values of MAX1 and MIN2 (or the MAX1/MIN2 ratio) with sensed values at the same frequencies until the difference (or ratio) is smaller than a predetermined threshold value, which indicates coagulation has been achieved. In addition, or alternatively, a table of impedance versus frequency curve points may be stored in memory and used for comparison purposes.

Figure 11D:
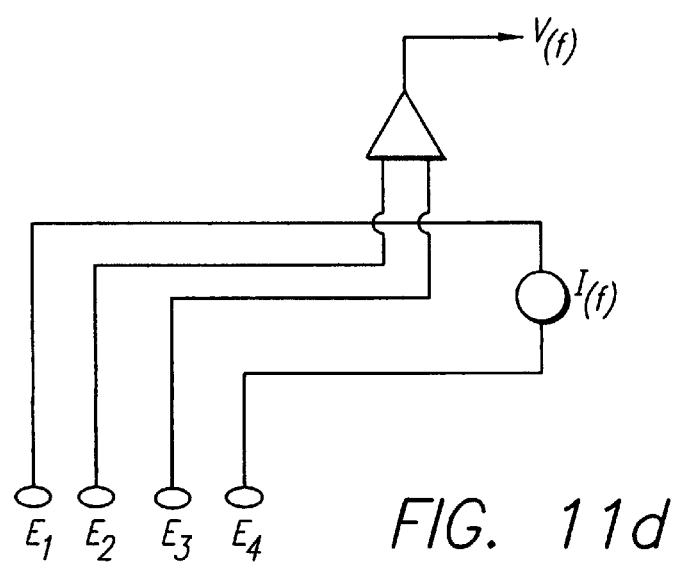
FIG. 11(d) is a schematic diagram of an impedance measurement technique.

As noted above, one method of measuring impedance involves measuring the voltage and current and dividing the measured voltage by the measured current. When using a probe having four spaced electrodes $E_1$-$E_4$, the technique illustrated in FIG. 11(d) may be used.

The particular f1 and f2 values and MAX1 and MIN2 values can vary according to tissue characteristics, as can the f1/f2 ratio and the MAX1/MIN2 ratio. For example, cardiac tissue and liver tissue may have different f1, f2, MAX1 or MIN2 values. This phenomenon is discussed in more detail in Rabbat A: Tissue resistivity. In Webster JG, ed: Electrical Impedance Tomography. Adam Hilger, Bristol, 1990. As such, impedance measurements may be used to determine tissue type. The tissue type determination may in turn be used both before and during a coagulation procedure to insure that the intended type of tissue will be and is being coagulated.

Additionally, if the impedance level exceeds 300 ohms, which is indicative of a situation where the electrodes are in air, then the energy level can be reduced to 5 V for a period of up to 10 seconds. The reduction can be either an immediate reduction or a ramping reduction. If the impedance level continues to exceed 300 ohms at the end of the period, then energy delivery will be stopped.

With respect to current, it can be used to both measure tissue contact and to prevent tissue charring and the formation of coagulum. For a given input maximum power level, there is a current level which, if reached, is either indicative of poor contact or of tissue charring and coagulum formation. For example, using 12.5 mm electrodes and a set power level of 70W, 0.9A is a preferable current limit, while 0.7A is a preferable limit when 6 mm electrodes are used with the same power setting.

Turning to temperature, prior to the coagulation procedure, a relatively small amount of energy (preferably about 20 V for 3 seconds) may be delivered to the tissue prior to the application of the larger amount of power necessary to coagulate tissue. The relatively small amount of power will increase the temperature of the tissue by a predetermined amount when the electrodes are in efficacious contact with the tissue. By comparing the sensed temperature rise to the expected temperature rise associated with efficacious contact (greater than or equal to about 1° C. per second), the processor can determine whether there is sufficient contact for the procedure to continue.

A temperature-based process may also be used to ascertain when tissue has been properly coagulated. Here, the controller monitors the sensed tissue temperature profile history (i.e. temperature over time) for a given power level. The temperature profile history is compared to a predetermined history for that power level stored in memory to determined when the coagulation process has ended. The controller will then cause the power circuit to end the delivery RF energy to the ablation electrode and, if desired, cause the console to provide an audio and/or visual indication that coagulation is complete.

As described above, certain aspects of the disclosed embodiments illustrated in FIGS. 1–10 combine negative feedback techniques with an automatic process controller. The controller (element 102 in FIG. 1 and element 331 in FIG. 3) compares sensed controlled variable data (such as temperature, impedance or current) to reference signal data, that is either input by the user or stored in memory, to generate an error signal. The error signal is used as input to the process controller that generates correcting influence on the feedback network circuit. The correcting influence can be used to affect the RF pulse train illustrated in FIG. 1. In the case of temperature feedback, the amount of energy delivered to the probe can be varied in order to maintain a temperature set point. In the cases of temperature, impedance and current, power can be ramped down to a predetermined level during a coagulation procedure when there is an indication that tissue contact is insufficient.

As discussed previously, the voltage output to the electrodes may be decreased from a higher level to a lower level upon a loss of tissue-electrode contact, as determined by the controller based on an error signal associated with measured temperature or impedance. The rate of RF voltage increase may also be limited upon resumption of coagulation to avoid tissue damage caused by overheating due to transient overshoot of high voltages. For example, voltage may be reduced to 5–20V if the measured temperature is more than 10° C. higher than the set temperature to avoid overheating or when there has been a loss of tissue-electrode contact. Once the overheating has been eliminated or contact has been reestablished, the power may be ramped back up to the level necessary to achieve the set temperature over a period of about 5 seconds.

V. Variable Temperature Set Point

In accordance with one of the present inventions, a variable temperature set point may be employed in a coagulation procedure. In other words, instead of immediately ramping up to the input desired maximum tissue temperature and maintaining that temperature, the controller first ramps tissue temperature up to at least one other temperature which is lower than the set maximum temperature. The controller then maintains that temperature for a predetermined period prior to increasing tissue temperature to the desired maximum temperature. This may be accomplished by, for example, using a PID temperature control algorithm with a temperature setpoint that varies over time, also referred to as a variable temperature set point curve.

The temperature at which tissue is maintained prior to ramping up to the input maximum temperature should be at least sufficient to desiccate tissue and is preferably sufficient to create a transmural lesion in a relatively thin tissue structure. The maximum temperature is preferably a temperature that will create a transmural lesion in a relatively thick structure. Thus, in those instances where the tissue structure turns out to be relatively thin, a transmural lesion may be completed (and power delivery stopped) before the temperature reaches the maximum temperature. The determination of lesion completion may be made through visual inspection or through the use of the techniques described above. Should the tissue structure turn out to be relatively thick, temperature will continue to ramp up to the maximum temperature.

Figure 13:
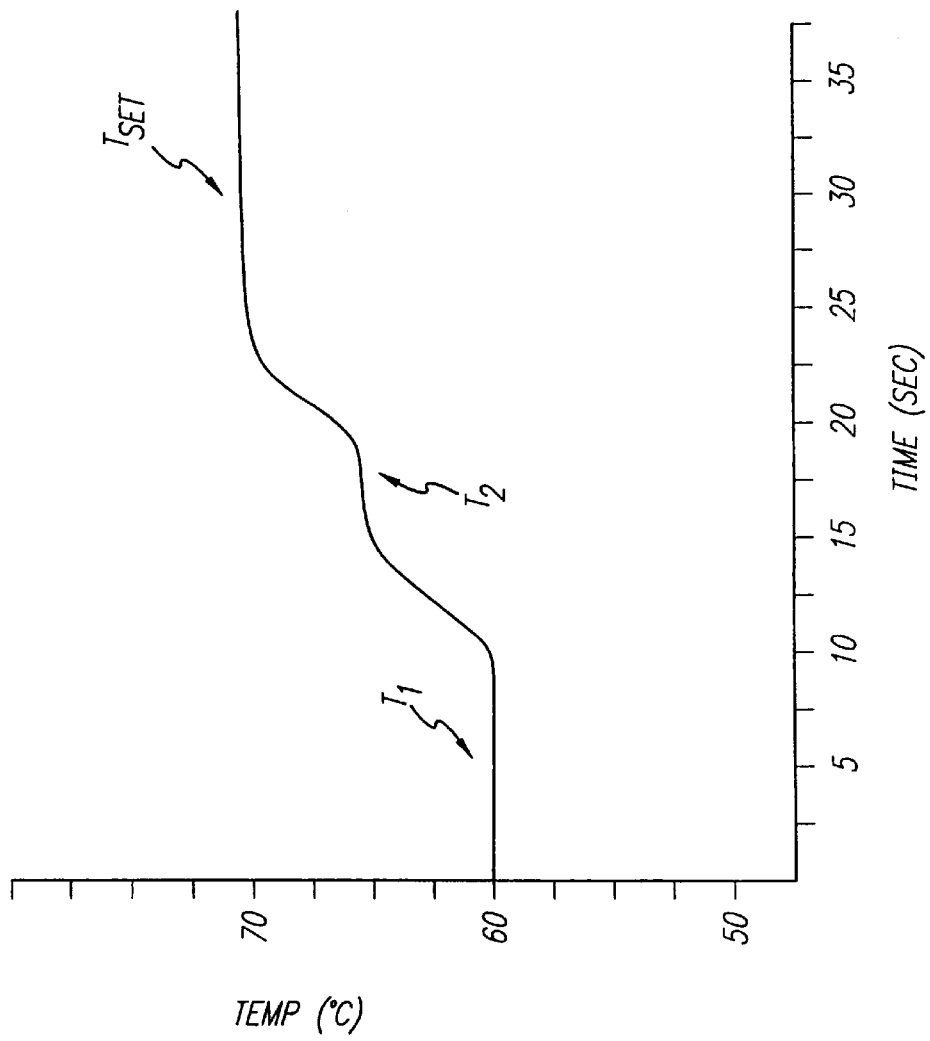
FIG. 13 is graph showing a variable temperature setpoint in accordance with a preferred embodiment of a present invention.

As shown by way of example in FIG. 13, one embodiment of the invention includes a temperature control algorithm wherein temperature is maintained at two different temperatures prior to reaching the set temperature $T_{SET}$. In the illustrated embodiment, the set point curve is based on a coagulation procedure where $T_{SET}$ is 70° C. and the total energy application time is 60 seconds. Both of these variables may be input by the physician. The controller initially sets the temperature setpoint at a first temperature $T_1$ for about 10 to 15 seconds. Temperature $T_1$ is about 10° C. less than $T_{SET}$. The controller then increases the temperature setpoint to a second temperature $T_2$ for about 10 seconds. Temperature $T_2$ is about 5° C. less than $T_{SET}$. Finally, the temperature setpoint is increased to the input temperature setpoint $T_{SET}$ for the remainder of the coagulation procedure.

The exemplary temperature set point curve described in the preceding paragraph is especially useful when creating a transmural lesion on the epicardial surface. Of course, other curves can be used in other situations. In endocardial applications where a transmural lesion is desired, for example, a temperature setpoint $T_{SET}$ of 70° C. may be necessary. The temperature set point curve used here preferably starts at a first temperature $T_1$ (about 60° C.) for about 10 to 15 seconds. Thereafter, the temperature setpoint increases at a rate of between about 1 and 2° C. per second until it reaches the input setpoint of 70° C. Other useful applications of the variable temperature setpoint include coagulation procedures where expandable (or "balloon") electrodes and other relatively large electrodes are used. Here, a setpoint curve wherein a first temperature setpoint $T_1$ (about 60° C.) was maintained for about 10 seconds and then increased at a rate of between about 1 and 2° C. per second until reaching an input setpoint of about 85° C. was found to be useful.

A variety of variable temperature setpoint curves that are specifically designed for a variety of procedures may be stored in the controller memory. Alternatively, or in addition, the controller may be provided with a program that generates a variable temperature setpoint curve based on input parameters such as maximum temperature, total energy application time, and type of procedure.

VI. User Interface System

One advantageous feature of the present user interface is that it will provide an indication that a therapeutic lesion has been successfully formed on the intended type of tissue. For example, some lesions will be formed based on information input by the physician via the user interface. The information may include lesion type, tissue type and type of probe (including electrode configuration). Probe type may also be automatically input by providing a device on the probe which is indicative of probe type in, for example, the manner disclosed in U.S. Pat. No. 5,743,903, which is incorporated herein by reference. The system controller will use these parameters to, for example, select a time variable set curve, the appropriate power level and a total energy application time. Of course, time, temperature, power level and other parameters can also input manually.

At the end of the input or automatically selected time period, the user interface will either instruct the operator to discontinue power application or simply indicate that power has been discontinued. The same operations may be performed in those instances where the controller determines that a therapeutic lesion has been formed based on, for example, tissue impedance measurements. Should the physician reach the point where there is an instruction to discontinue power (or power is automatically discontinued) without an error signal (such as loss of contact) he or she will know that a therapeutic lesion has been formed. Alternatively, an audible or visual indication may be provided when a therapeutic lesion has been successfully formed.

In accordance with one embodiment of the invention, software drives the processor 102 to operate the coagulation processes described above. Such software will also drive operation of a user interface, such as the console 103 illustrated in FIGS. 1 and 2, which provides information obtained before and during the coagulation procedure.

A flow chart illustrating the steps performed by the exemplary software is illustrated in FIG. 12. The software may be written in any standard industry software language, such as the C or C++ languages. It is contemplated that the software is executable code residing in RAM, or may be part of a dedicated processor existing as firmware, ROM, EPROM or the like. The steps listed in the program correspond to, inter alia, function calls, modules, subroutines, classes, and/or lines of executable code in a machine readable program operating a general purpose microprocessor and, therefore, constitute apparatus for executing such steps in addition to methods of operation.

In step 501, the software program performs a power-on self test. Here, the program checks to see whether the supply voltages are within the specified range, whether the front panel console and remote LEDs are functional, etc. In step 503, the initial selected values are displayed by the console. Such values may include a set tissue temperature with, for example, an initial default value of 70° C. and measured values from the sensors. Step 505 is the start of the switch checking process. In step 507, the application of RF energy is started if the RF energy ON switch is depressed. Otherwise, the power up/down switch is checked (step 509), and if that switch is depressed, the upper power limit allowed for the power supply is adjusted as necessary in step 511. If the power up/down switch is not depressed, the temperature up/down switch is checked (step 513) and the temperature setpoint is adjusted as necessary in step 515. If the temperature up/down switch is not depressed, the process loops back to step 505.

In step 517, which follows a RF energy ON finding in step 507, the ablation process begins. Here, an "RF energy ON" signal is provided by the console and an audible tone emitted. The global power ON/OFF switch(es) are checked in step 519, such as a foot pedal switch or switch on a remote control device. In step 521, the processor checks for electrode contact verification between the electrodes and tissue and, if there is contact (step 523), proceeds to step 525. Otherwise, the coagulation process is either stopped by ramping down power to a predetermined level, disabling a selected electrode or, if the process has yet to begin, simply not started. Audio and/or visual signals concerning the lack of suitable contact are then activated (step 527) and the software returns to step 503.

If the RF power ON switch is still activated in step 525, the power increment UP/DOWN switch is checked (step 529). Otherwise, the program returns to step 527. If the power increment UP/DOWN switch is depressed, step 531 is pursued to adjust the power limit, while continuing the coagulation process, and the return path 533 is taken to step 519. If the power increment UP/DOWN switch has not been depressed, the temperature UP/DOWN switch is checked (step 535). The temperature setpoint is adjusted in step 537, while continuing the coagulation process, and then returning to step 519.

Additional and optional steps may be added to the software after step 535. [Note steps 540 and 545.] Such additional steps may, for example, include determining whether or not a probe has been attached to the power supply and control apparatus, determining the elapsed time of coagulation, determining the power outputted. Other additional steps include providing an audible tone at a predetermined interval, such as every 30 seconds, and displaying the probe type. Also, at each and every step, the processor may refresh the console display with relevant data that is displayed.

This specification discloses multiple electrode structures in the context of cardiac tissue coagulation because the structures are well suited for use in the field of cardiac treatment. Nevertheless, it should be appreciated that the disclosed structures are applicable for use in other applications. For example, various aspects of the invention have applications and procedures concerning other regions of the body such as the prostate, brain, gall bladder and uterus.

Although the present invention has been described in terms of the preferred embodiments above, numerous modifications and/or additions to the above-described preferred embodiments would be readily apparent to one skilled in the art. It is intended that the scope of the present invention extends to all such modifications and/or additions and that the scope of the present invention is limited solely by the claims set forth below.

We claim:

1. An apparatus for coagulating tissue, comprising:
   a support element;
   at least one operative element on the support element; and
   a control system, operably connected to the operative element, and adapted to measure impedance and determine whether the operative element is in contact with tissue and whether tissue in proximity to the operative element is viable tissue or non-viable tissue, at least one of the determinations being based on an impedance versus frequency profile.

2. An apparatus as claimed in claim 1, wherein the contact determination is based on the impedance versus frequency profile.

3. An apparatus as claimed in claim 1, wherein the viability determination is based on the impedance versus frequency profile.

4. An apparatus as claimed in claim 1, wherein the operative element comprises an electrode.

5. An apparatus as claimed in claim 1, wherein the control system is adapted to generate at least one of an audio alarm and a visual alarm in response to at least one of a non-viable tissue determination and a loss of contact determination.

6. An apparatus as claimed in claim 1, wherein the support element comprises a relatively stiff shaft.

7. An apparatus as claimed in claim 1, wherein the control system determines whether the operative element is in contact with viable tissue prior to initiating a coagulation procedure.

8. An apparatus for coagulating tissue, comprising:
   a support element;
   at least one operative element on the support element; and
   a control system, operably connected to the operative element, that measures temperature at the operative element and determines whether the operative element is in contact with tissue and whether tissue in proximity to the operative element is viable tissue or non-viable tissue, at least one of the determinations being based on the temperature measurement.

9. An apparatus as claimed in claim 8, wherein the operative element comprises an electrode.

10. An apparatus as claimed in claim 8, wherein the control system is adapted to generate at least one of an audio alarm and a visual alarm in response to at least one of a non-viable tissue determination and a loss of contact determination.

11. An apparatus as claimed in claim 8, wherein the support element comprises a relatively stiff shaft.

12. An apparatus as claimed in claim 8, wherein the control system determines whether the operative element is in contact with viable tissue prior to initiating a coagulation procedure.

13. An apparatus for coagulating tissue, comprising:
   a support element;
   at least one electrode on the support element;
   a source of tissue coagulating energy operably connected to the electrode and adapted to supply energy at a first level suitable for tissue coagulation and at a second, non-zero level lower than the first level; and
   a control system, operably connected to the electrode, and adapted to determine whether the electrode is in contact with tissue and whether tissue in proximity to the electrode is viable tissue or non-viable tissue and to reduce the energy level from the first level to the second level in response to the loss of contact determination.

14. An apparatus as claimed in claim 13, wherein the energy source comprises a radio frequency energy source.

15. An apparatus as claimed in claim 13, wherein the control system causes the energy source to ramp down to the second level in response to the loss of contact determination.

16. An apparatus as claimed in claim 13, wherein the control system causes the energy source to ramp up to the first level in response a determination that contact between the at least one electrode and tissue has been reestablished.

17. A method of coagulating tissue, comprising the steps of:
attempting to place an operative element in at least close proximity to tissue;
performing a first data sensing operation to sense impedance data at various frequencies;
comparing the impedance data to an impedance versus frequency profile to determine one of whether the electrode is in contact with tissue and whether tissue in proximity to the electrode is viable tissue or non-viable tissue;
performing a second data sensing operation; and
using the data sensed during the second data sensing operation to determine the other of whether the electrode is in contact with tissue and whether tissue in proximity to the electrode is viable tissue or non-viable tissue.

18. A method as claimed in claim 13, wherein the impedance data is used to determine whether the operative element is in contact with tissue.

19. A method as claimed in claim 13, wherein the impedance data is used to determine whether the tissue is viable tissue or non-viable tissue.

20. A method of coagulating tissue, comprising the steps of:
attempting to place an operative element in at least close proximity to tissue;
performing a first data sensing operation to sense temperature data;
using the temperature data to determine whether the tissue is viable tissue or non-viable tissue; and
performing a second data sensing operation to determine whether the operative element is in contact with the tissue.

21. An apparatus for coagulating tissue, comprising:
a support element;
at least one tissue heating element on the support element;
at least one temperature sensor on the support element;
a source of tissue heating energy operably connected to the tissue heating element and adapted to supply energy at a first level suitable for tissue coagulation and at a second, non-zero level lower than the first level, the second level being suitable to heat tissue with a predetermined rate of temperature rise when the tissue heating element is in contact with the tissue; and
a control system, operably connected to the at least one temperature sensor, and adapted to determine whether the tissue heating element is in contact with the tissue based on feedback from the temperature sensor.

22. An apparatus as claimed in claim 13, wherein the control system is adapted to cause the energy source to provide energy to the at least one tissue heating element at the second level, receive a temperature signal from the at least one temperature sensor, and determine whether the tissue heating element is in contact with the tissue by determining whether the temperature has reached the predetermined temperature.

23. An apparatus as claimed in claim 22, wherein the control system is adapted to cause the energy source to provide energy at the first level in response a determination that the tissue has reached the predetermined temperature.

24. An apparatus as claimed in claim 22, wherein the control system will not cause the energy source to provide energy at the first level until a determination that the tissue has reached the predetermined temperature.

25. An apparatus as claimed in claim 22, wherein the control system is adapted to generate at least one of an audio alarm and a visual alarm in response to a determination that tissue did not reach the predetermined temperature in response to an application of energy at the second level.

26. An apparatus as claimed in claim 21, wherein the support element comprises a relatively stiff shaft.

27. An apparatus as claimed in claim 21, wherein the tissue heating element comprises an electrode.

28. An apparatus as claimed in claim 21, wherein the source of tissue heating energy comprises a source of RF energy.

29. A method of coagulating tissue, comprising the steps of:
attempting to place a tissue heating element in contact with tissue;
supplying the tissue heating element with energy at a first level insufficient to coagulate the tissue and sufficient to cause the tissue to rise to a predetermined temperature level when the tissue heating element is in contact with the tissue;
sensing the temperature of the tissue; and
determining whether the tissue heating element is in contact with tissue based on the sensed temperature of the tissue.

30. A method as claimed in claim 29, further comprising the step of:
supplying the tissue heating element with energy at a second level sufficient to coagulate tissue in response to a determination that the tissue heating element is in contact with tissue.

31. A method as claimed in claim 21, wherein the step of determining whether the tissue heating element is in contact with tissue comprises determining whether the temperature of the tissue rises at a predetermined rate.

32. An apparatus for coagulating tissue, comprising:
a support element;
at least one electrode on the support element;
a source of tissue coagulating energy operably connected to the electrode and adapted to supply energy at a first voltage suitable for tissue coagulation and at a second, non-zero voltage lower than the first voltage; and
a control system, operably connected to energy source, and adapted to determine when there is a loss of contact between the at least one electrode and tissue and to reduce the voltage level from the first voltage to the second voltage in response to the loss of contact determination.

33. An apparatus as claimed in claim 32, wherein the control system causes the energy source to ramp down to the second voltage in response to the loss of contact determination.

* * * * *

UNITED STATES PATENT AND TRADEMARK OFFICE
CERTIFICATE OF CORRECTION

PATENT NO.   : 6,123,702
DATED        : September 26, 2000
INVENTOR(S)  : David K. Swanson et al.

It is certified that error appears in the above-identified patent and that said Letters Patent is hereby corrected as shown below:

Column 23,
Line 29, replace "13" with -- 17 --.
Line 32, replace "13" with -- 17 --.
Line 63, replace "13" with -- 21 --.

Column 24,
Line 44, replace "21" with -- 29 --.

Signed and Sealed this

Fifteenth Day of October, 2002

Attest:

JAMES E. ROGAN
Attesting Officer       Director of the United States Patent and Trademark Office